US009816148B2

(12) United States Patent
Umansky et al.

(10) Patent No.: US 9,816,148 B2
(45) Date of Patent: Nov. 14, 2017

(54) AMPLIFICATION AND SEQUENCING OF TRANSRENAL NUCLEIC ACIDS

(71) Applicant: Trovagene, Inc., San Diego, CA (US)

(72) Inventors: Samuil R. Umansky, Princeton, NJ (US); Hovsep S. Melkonyan, Princeton, NJ (US); Eugene M. Shekhtman, Plainsboro, NJ (US)

(73) Assignee: Trovagene, Inc., San Diego, CA (US)

( * ) Notice: Subject to any disclaimer, the term of this patent is extended or adjusted under 35 U.S.C. 154(b) by 0 days.

(21) Appl. No.: 14/819,692

(22) Filed: Aug. 6, 2015

(65) Prior Publication Data
US 2015/0329920 A1 Nov. 19, 2015

Related U.S. Application Data

(63) Continuation of application No. 13/898,449, filed on May 20, 2013, which is a continuation of application No. 12/505,183, filed on Jul. 17, 2009.

(60) Provisional application No. 61/135,364, filed on Jul. 18, 2008.

(51) Int. Cl.
*C12Q 1/68* (2006.01)
*C12Q 1/70* (2006.01)

(52) U.S. Cl.
CPC .......... *C12Q 1/705* (2013.01); *C12Q 1/6806* (2013.01); *C12Q 1/6846* (2013.01); *C12Q 1/6851* (2013.01); *C12Q 1/6886* (2013.01); *C12Q 2600/106* (2013.01); *C12Q 2600/156* (2013.01); *C12Q 2600/158* (2013.01)

(58) Field of Classification Search
None
See application file for complete search history.

(56) References Cited

U.S. PATENT DOCUMENTS

| | | | |
|---|---|---|---|
| 4,148,319 A | 4/1979 | Kasper et al. | |
| 6,251,638 B1 * | 6/2001 | Umansky | C12Q 1/6806 435/6.1 |
| 6,287,820 B1 * | 9/2001 | Umansky | C12Q 1/6806 435/6.1 |
| 6,492,144 B1 | 12/2002 | Umansky et al. | |
| 6,905,827 B2 | 6/2005 | Wohlgemuth et al. | |
| 7,101,663 B2 | 9/2006 | Godfrey et al. | |
| 7,442,506 B2 | 10/2008 | Dhallan | |
| 2002/0146735 A1 | 10/2002 | Franzen | |
| 2002/0197611 A1 * | 12/2002 | Chagovetz | C12Q 1/6851 435/6.11 |
| 2003/0113781 A1 * | 6/2003 | Bortolin | C12Q 1/6813 435/6.11 |
| 2006/0068417 A1 * | 3/2006 | Becker | C12Q 1/6834 435/6.11 |
| 2006/0228721 A1 | 10/2006 | Leamon et al. | |
| 2006/0292616 A1 * | 12/2006 | Neely | C12Q 1/6886 435/6.12 |
| 2007/0059690 A1 * | 3/2007 | Islam | C12Q 1/6818 435/6.12 |
| 2007/0065844 A1 * | 3/2007 | Golub | C12Q 1/6834 435/6.14 |
| 2007/0072204 A1 * | 3/2007 | Hannon | C12N 15/1135 435/6.14 |
| 2007/0117125 A1 * | 5/2007 | Chemeris | C12Q 1/686 435/6.18 |
| 2007/0258898 A1 | 11/2007 | Ballinger et al. | |
| 2008/0020390 A1 * | 1/2008 | Mitchell | C12Q 1/6883 435/6.12 |
| 2008/0139801 A1 * | 6/2008 | Umansky | C12N 15/101 536/25.41 |
| 2009/0081640 A1 * | 3/2009 | Umansky | C12Q 1/6883 435/5 |
| 2009/0209621 A1 * | 8/2009 | Mendell | C12N 15/113 514/44 A |
| 2009/0275632 A1 * | 11/2009 | Esteller | C12Q 1/6809 514/44 A |
| 2010/0151468 A1 * | 6/2010 | Esteller | C12Q 1/6886 435/6.12 |
| 2016/0010163 A1 * | 1/2016 | Preston | C12Q 1/6806 506/2 |

FOREIGN PATENT DOCUMENTS

| | | | |
|---|---|---|---|
| WO | 9854364 | 12/1998 | |
| WO | 2005003375 A2 | 1/2005 | |
| WO | 2005012523 A1 | 2/2005 | |
| WO | 2006089203 A2 | 8/2006 | |
| WO | WO 2006088895 A2 * | 8/2006 | ........... C12Q 1/6806 |
| WO | 2007100911 A2 | 9/2007 | |
| WO | WO 2007140417 A2 * | 12/2007 | ......... C12N 15/1003 |
| WO | WO 2008008430 A2 * | 1/2008 | ........... C12Q 1/6809 |
| WO | 2008029295 A2 | 3/2008 | |

(Continued)

OTHER PUBLICATIONS

Ahmad et al. (New FRET primers for quantitative real-time PCR, Anal Bioanal Chem. Apr. 2007;387(8):2737-43. Epub Feb. 17, 2007).*
Sharbati-Tehrani et al. (miR-Q: a novel quantitative RT-PCR approach for the expression profiling of small RNA molecules such as miRNAs in a complex sample, BMC Molecular Biology 2008, 9:34, Apr. 10, 2008).*
Su et al. (Human Urine Contains Small, 150 to 250 Nucleotide-Sized, Soluble DNA Derived from the Circulation and May Be Useful in the Detection of Colorectal Cancer, J Mol Diagn. May 2004;6(2):101-7).*
Shekhtman et al. (Optimization of Transrenal DNA Analysis: Detection of Fetal DNA in Maternal Urine, Clin Chem. Apr. 2009;55(4):723-9. doi: 10.1373/clinchem.2008.113050. Epub Jan. 30, 2009).*
Melkonyan et al. (Transrenal Nucleic Acids: From Proof of Principle to Clinical Tests: Problems and Solutions, Annals of the New York Academy of Sciences, vol. 1137, Circulating Nucleic Acids in Plasma and Serum V, pp. 73-81, Aug. 1, 2008).*
Chen et al. (Real-time quantification of microRNAs by stem-loop RT-PCR, Nucleic Acids Res. Nov. 27, 2005;33(20):e179).*

(Continued)

*Primary Examiner* — Aaron Priest
(74) *Attorney, Agent, or Firm* — Holly Logue; Elie Gendloff; Lewis Roca Rothgerber Christie LLP

(57) ABSTRACT

The present invention provides highly sensitive methods used for diagnosing and monitoring various diseases and disorders by detecting and analyzing "ultra short" (20-50 base pair) nucleic acids obtained from bodily fluids.

18 Claims, 15 Drawing Sheets

(56) References Cited

FOREIGN PATENT DOCUMENTS

| WO | 2008045505 | 4/2008 |
|---|---|---|
| WO | 2009025852 | 2/2009 |

OTHER PUBLICATIONS

Ro et al. (A PCR-based Method for Detection and Quantification of Small RNAs, Biochem Biophys Res Commun. Dec. 22, 2006;351(3): 756-763).*
Koide et al. (Fragmentation of cell-free fetal DNA in plasma and urine of pregnant women, Prenat Diagn. Jul. 2005;25(7):604-7).*
Chan et al. (Quantitative Analysis of the Trans-renal Excretion of Circulating EBV DNA in Nasopharyngeal Carcinoma Patients, Clin Cancer Res. Aug. 1, 2008;14(15):4809-13).*
Bryzgunova et al. (Isolation and Comparative Study of Cell-Free Nucleic Acids from Human Urine, Ann N Y Acad Sci. Sep. 2006;1075:334-40).*
Hung et al. (Presence of Donor-Derived DNA and Cells in the Urine of Sex-Mismatched Hematopoietic Stem Cell Transplant Recipients: Implication for the Trans-renal Hypothesis, Clin Chem. Apr. 2009;55(4):715-22. doi: 10.1373/clinchem.2008.113530. Epub Oct. 30, 2008).*
Hanke et al. (A robust methodology to study urine microRNA as tumor marker: microRNA-126 and microRNA-182 are related to urinary bladder cancer, Urol Oncol. Nov.-Dec. 2010;28(6):655-61. doi: 10.1016/j.urolonc.2009.01.027. Epub Apr. 17, 2009).*
Kemppainen et al. (microRNAs as Biomarkers in Blood and Other Biofluids, attached, available at http://asuragen.com/pdfs/posters/biomarkers.pdf, Mar. 29, 2007).*
Rickert et al. (Multiplexed Real-Time PCR Using Universal Reporters, Clin Chem. Sep. 2004;50(9):1680-3).*
Butler et al. (The development of reduced size STR amplicons as tools for analysis of degraded DNA, J Forensic Sci. Sep. 2003:48(5):1054-64).*
Gundry et al. (Base-pair neutral homozygotes can be discriminated by calibrated high-resolution melting of small amplicons, Nucleic Acids Res. Jun. 2008;36(10):3401-8. doi: 10.1093/nar/gkn204. Epub Apr. 29, 2008).*
Liew et al. (Genotyping of single-nucleotide polymorphisms by high-resolution melting of small amplicons, Clin Chem. Jul. 2004:50(7):1156-64).*
Umansky & Tomei (Transrenal DNA testing: progress and perspectives, Expert Rev Mol Diagn. Mar. 2006;6(2):153-63).*
Utting et al. (Microsatellite analysis of free tumor DNA in urine, serum, and plasma of patients: a minimally invasive method for the detection of bladder cancer, Clin Cancer Res. Jan. 2002;8(1):35-40).*
GE Healthcare (Q Sepharose High Performance SP Sepharose High Performance, attached, Apr. 2006).*
Chan, K.C.A. et al., Quantitative Analysis of the Transrenal Excretion of Circulating EBV DNA in Nasopharyngeal Carcinoma Patients, Imaging, Diagnosis Prognosis, vol. 14(15), Aug. 1, 2008, pp. 4809-4813.
Chiu, R.W.K., et al., Noninvasive prenatal diagnosis of fetal chromosomal aneuploidy by massively parallel genomic sequencing of DNA in maternal plasma, PNAS, Dec. 23, 2008, vol. 105, No. 51, pp. 20458-20463.
Fan, H.C., et al., Noninvasive diagnosis of fetal aneuploidy by shotgun sequencing DNA from maternal blood, PNAS, Oct. 21, 2008, vol. 105, No. 42, pp. 16266-16271.
Hafner, M., et al., Identification of microRNAs and other small regulatory RNAs using cDNA library sequencing, ScienceDirect, Methods 44, 2008, pp. 3-12.
Koide, K., et al., Fragmentation of cell-free fetal DNA in plasma and urine of pregnant women, Prenatal Diagnosis, 2005, vol. 25, pp. 604-607.
Korshunova, Y. et al., Massively parallel bisulphite pyrosequencing reveals the molecular complexity of breast cancer-associated cytosine-methylation patterns obtained from tissue and serum DNA, Letter, Genome Research, 2008, pp. 19-29.
Lo, Y.M.D. et al., Next Generation Sequencing of Plasma/Serum DNA: An Emerging Research and Molecular Diagnostic Tool, Editorials, Clinical Chemistry, vol. 55:4, 2009, pp. 607-608.
Poon, L.L,M. et al., Differential DNA Methylation between Fetus and Mother as a Strategy for Detecgting Fetal DNA in Maternal Plasma, Molecular Diagnostics and Genetics, Clinical Chemistry, vol. 48:1, 2002, pp. 35-41.
Suzuki, N. et al., Characterization of circulating DNA in healthy human plasma, ScienceDirect, Clinica Chimica Acta, vol. 387, 2008, pp. 55-58.
Van der Vaart, M. et al., A Method for Characterization of Total Circulating DNA, Annals of the New York Academy of Sciences, vol. 1137, 2008, pp. 92-97.
Voelkerding, K.V. et al., Next-Generation Sequencing: From Basic Research to Diagnostics, Reviews, Clinical Chemistry vol. 55:4, 2009, pp. 641-658.
Li, Ying et al., "Inability to Detect Cell Free Fetal DNA in the Urine of Normal Pregnant Woman nor in Those Affected by Preeclampsia Associated HELLP Syndrome", J. Soc. Gynecol. Investig., vol. 10, No. 8, Dec. 2003, 503-508.
Llanes, S. et al., "Detection of cell-free fetal DNA in maternal urine", Prenatal Diagnosis, 2006, 26:1216-1218.
Sommer, R. et al., "Minimal homology requirements for PCR primers", Nucleic Acids Research, vol. 17, No. 16, 1989, p. 6749.
Ameisen, JC, "Looking for Death at the Core of Life in the Light of Evolution", Cell Death and Diff., 2004, No. 11, pp. 4-10.
Arends, M.J. et al., "Apoptosis: The Role of the Endonuclease", Am. J. Pathol., vol. 136, No. 3 (1990), pp. 593-608.
Bischoff, F. Z. et al., "Cell-Free Fetal DNA and Intact Fetal Cells in Maternal Blood Circulation: Implications for First and Second Trimester Non-Invasive Prenatal Diagnosis", Hum. Reprod. Update, vol. 8, No. 6 (2002), pp. 493-500.
Cannas, A. et al., "*Mycobacterium tuberculosis* DNA Detection in Soluble Fraction of Urine From Pulmonary Tuberculosis Patients", Int. J. Tuberc. Lung Dis., 12(2):146-151 (2008).
Chan, K.C. Allen et al., "Circulating EBV DNA as a Tumor Marker for Nasopharyngeal Carcinoma", Semin. Cancer Biol. 12(6):489-496 (2002).
Chan, K.E. Allen et al., "Molecular Characterization of Circulating EBV DNA in the Plasma of Nasopharyngeal Carcinoma and Lymphoma Patients", Cancer Res. 63:2028-2032 (2003).
Diehl, F. et al., "Analysis of Mutations in DNA Isolated From Plasma and Stool of Colorectal Cancer Patients", Gastroenterol. 135.2(2008):489-498.
Ding, C. et al., "MS Analysis of Single-Nucleotide Differences in Circulating Nucleic Acids: Application to Noninvasive Prenatal Diagnosis", PNAS (2004), vol. 101, No. 29, pp. 10762-10767.
Goessi, C. et al., "Diagnostic Potential of Circulating Nucleic Acids for Oncology", Expert Rev. Mol. Diagn. 3(4):431-442 (2003).
Kerr, J.F.R. et al., "Apoptosis: A Basic Biological Phenomenon With Wide-Ranging Implications in Tissue Kinetics", Br. J. Cancer. (1972), 26(4):239-257.
Kroemer, G. et al., "Classification of Cell Death: Recommendations of the Nomenclature Committee on Cell Death", Cell Death Differ. (2005) 12:1463-1467.
Lichtenstein, A. V. et al., "Circulating Nucleic Acids and Apoptosis", Ann. NY Acad. Sci. (2001), 945:239-249.
Lo, Y.M. Dennis et al., "Prenatal Diagnosis: Progress Through Plasma Nucleic Acids", Nat. Rev. Genet., vol. 8 (2004):71-77.
Lo, Y.M. Dennis, "Circulating Nucleic Acids in Plasma and Serum: An Overview", Ann. NY Acad. Sci., vol. 945 (2001):1-7.
Lockshin, R. A. et al., "Apoptosis, Autophagy, and More", Int. J. Biochem. Cell Biol., vol. 36, No. 12 (2004):2405-2419.
Su, Y. H. et al., "Human Urine Contains Small, 150 to 250 Nucleotide-Sized, Soluble DNA Derived From the Circulation and May be Useful in the Detection of Colorectal Cancer", J. Mol. Diagn., vol. 6, No. 2 (2004):101-107.
Taback B. et al., "Circulating Nucleic Acids in Plasma and Serum: Past, Present and Future", Curr. Opin. Mol. Ther., vol. 6, No. 3 (2004):273-278.
Tsang, J.C.H. et al., "Circulating Nucleic Acids in Plasma/Serum", Pathol., vol. 39, No. 2 (2007):197-207.

(56) References Cited

OTHER PUBLICATIONS

Tsui, N. B. Y et al., "Placental RNA in Maternal Plasma: Toward Noninvasive Fetal Gene Expression Profiling", Ann. NY. Acad. Sci. 1075(2006):96-102.
Umansky, S. et al., "Apoptosis in the Heart", Adv. Pharmcol. 41(1997):383-407.
Umansky, S. et al. "In vivo DNA Degradation in Thymocytes of y-Irradiated or Hydrocortisone-Treated Rats", Biochim. Biophys. Acta. 655.1(1981):9-17.
Umansky, S. "The Genetic Program of Cell Death", J. Theor. Biol. 97.4(1982):591-602.
Wataganara T. et al., "Fetal Cell-Free Nucleic Acids in the Maternal Circulation: New Clinical Applications", Ann. NY. Acad. Sci. 1022(2004):90-99.
Zimmerman K. C. et al., "The Machinery of Programmed Cell Death", Pharmacol. Ther. 92.1(2001):57-70.
Melkonyan, H.S. et al., "Transrenal Nucleic Acids: From Proof of Principle to Clinical Tests," Annals New York Academy of Sciences, Sep. 16, 2008 (online), vol. 1137, pp. 73-81.
Unknown, "Virus," Wikipedia.com, accessed Apr. 18, 2012 at http://en.wikipedio.org/wiki/virus.
Unknown, "How many species of bacteria are there?" Wisegeek.com, accessed Sep. 23, 2011 at http://www.wisegeek.com/how-many-species-of-bacteria-are-there.htm.
Ahmad A. I. et al., "New FRET primers for quantitative real-time PCR", Anal Bioanal Chem., (2007), 387:2737-43.
Botezatu I. et al., "Genetic analysis of DNA excreted in urine: a new approach for detecting specific genomic DNA sequences from cells dying in an organism", Clin. Chem. 46:8, pp. 1078-1084 (2000).
Su, Y.H., "Transrenal DNA as a diagnostic tool: important technical notes", Ann N Y Acad Sci. 1022: 81-9 (2004).

\* cited by examiner

SEQUENCE LISTING

<160> NUMBER OF SEQ ID NOS: 27

<210> SEQ ID NO 1
<211> LENGTH: 20
<212> TYPE: DNA
<213> ORGANISM: Artificial Sequence
<220> FEATURE:
<223> OTHER INFORMATION: primer sequence
<220> FEATURE:
<221> NAME/KEY: modified_base
<222> LOCATION: (18)..(18)
<223> OTHER INFORMATION: wherein t is modified by 6-carboxyfluorescein (FAM)

<400> SEQUENCE: 1
cgtccgtgct gtcgacgtag                                          20

```
<210> SEQ ID NO 2
<211> LENGTH: 21
<212> TYPE: DNA
<213> ORGANISM: Artificial Sequence
<220> FEATURE:
<223> OTHER INFORMATION: primer sequence
<220> FEATURE:
<221> NAME/KEY: modified_base
<222> LOCATION: (18)..(18)
<223> OTHER INFORMATION: wherein t is modified by carboxy-X-rhodamine
      (ROX)

<400> SEQUENCE: 2
cataccacgc catcagagtg c                                              21

<210> SEQ ID NO 3
<211> LENGTH: 33
<212> TYPE: DNA
<213> ORGANISM: Artificial Sequence
<220> FEATURE:
<223> OTHER INFORMATION: primer sequence

<400> SEQUENCE: 3
cagcacgtcc gtgctgtcga cgtagacatc agc                                 33

<210> SEQ ID NO 4
<211> LENGTH: 24
<212> TYPE: DNA
<213> ORGANISM: Artificial Sequence
<220> FEATURE:
<223> OTHER INFORMATION: primer sequence

<400> SEQUENCE: 4
actctgatgg cgtggtatga cgac                                           24

<210> SEQ ID NO 5
<211> LENGTH: 32
<212> TYPE: DNA
<213> ORGANISM: Artificial Sequence
<220> FEATURE:
<223> OTHER INFORMATION: primer sequence

<400> SEQUENCE: 5
cagcacgtcc gtgctgtcga cgtagcatca gc                                  32

<210> SEQ ID NO 6
<211> LENGTH: 24
<212> TYPE: DNA
<213> ORGANISM: Artificial Sequence
<220> FEATURE:
<223> OTHER INFORMATION: primer sequence

<400> SEQUENCE: 6
actctgatgg cgtggtatga cgac                                           24

<210> SEQ ID NO 7
<211> LENGTH: 31
<212> TYPE: DNA
<213> ORGANISM: Artificial Sequence
<220> FEATURE:
<223> OTHER INFORMATION: primer sequence

<400> SEQUENCE: 7
cagcacgtcc gtgctgtcga cgtagatcag c                                   31
```

-continued

```
<210> SEQ ID NO 8
<211> LENGTH: 24
<212> TYPE: DNA
<213> ORGANISM: Artificial Sequence
<220> FEATURE:
<223> OTHER INFORMATION: primer sequence

<400> SEQUENCE: 8
actctgatgg cgtggtatga cgac                                            24

<210> SEQ ID NO 9
<211> LENGTH: 29
<212> TYPE: DNA
<213> ORGANISM: Artificial Sequence
<220> FEATURE:
<223> OTHER INFORMATION: primer sequence

<400> SEQUENCE: 9
cagcacgtcc gtgctgtcga cgtagatgc                                       29

<210> SEQ ID NO 10
<211> LENGTH: 24
<212> TYPE: DNA
<213> ORGANISM: Artificial Sequence
<220> FEATURE:
<223> OTHER INFORMATION: primer sequence

<400> SEQUENCE: 10
actctgatgg cgtggtatga cgac                                            24

<210> SEQ ID NO 11
<211> LENGTH: 28
<212> TYPE: DNA
<213> ORGANISM: Artificial Sequence
<220> FEATURE:
<223> OTHER INFORMATION: primer sequence

<400> SEQUENCE: 11
cagcacgtcc gtgctgtcga cgtagagc                                        28

<210> SEQ ID NO 12
<211> LENGTH: 24
<212> TYPE: DNA
<213> ORGANISM: Artificial Sequence
<220> FEATURE:
<223> OTHER INFORMATION: primer sequence

<400> SEQUENCE: 12
actctgatgg cgtggtatga cgac                                            24

<210> SEQ ID NO 13
<211> LENGTH: 27
<212> TYPE: DNA
<213> ORGANISM: Artificial Sequence
<220> FEATURE:
<223> OTHER INFORMATION: primer sequence

<400> SEQUENCE: 13
cagcacgtcc gtgctgtcga cgtaggc                                         27

<210> SEQ ID NO 14
<211> LENGTH: 24
<212> TYPE: DNA
<213> ORGANISM: Artificial Sequence
<220> FEATURE:
<223> OTHER INFORMATION: primer sequence
```

```
<400> SEQUENCE: 14
actctgatgg cgtggtatga cgac                                            24

<210> SEQ ID NO 15
<211> LENGTH: 25
<212> TYPE: DNA
<213> ORGANISM: Artificial Sequence
<220> FEATURE:
<223> OTHER INFORMATION: primer sequence

<400> SEQUENCE: 15
cagcacgtcc gtgctgtcga cgtac                                           25

<210> SEQ ID NO 16
<211> LENGTH: 24
<212> TYPE: DNA
<213> ORGANISM: Artificial Sequence
<220> FEATURE:
<223> OTHER INFORMATION: primer sequence

<400> SEQUENCE: 16
actctgatgg cgtggtatga cgac                                            24

<210> SEQ ID NO 17
<211> LENGTH: 21
<212> TYPE: DNA
<213> ORGANISM: Artificial Sequence
<220> FEATURE:
<223> OTHER INFORMATION: primer sequence
<220> FEATURE:
<221> NAME/KEY: modified_base
<222> LOCATION: (19)..(19)
<223> OTHER INFORMATION: wherein t is modified by 6-carboxyfluorescein
      (FAM)

<400> SEQUENCE: 17
atcgcagagc ccaggatgtc c                                               21

<210> SEQ ID NO 18
<211> LENGTH: 23
<212> TYPE: DNA
<213> ORGANISM: Artificial Sequence
<220> FEATURE:
<223> OTHER INFORMATION: primer sequence
<220> FEATURE:
<221> NAME/KEY: modified_base
<222> LOCATION: (21)..(21)
<223> OTHER INFORMATION: wherein t is modified by carboxy-X-rhodamine
      (ROX)

<400> SEQUENCE: 18
acgagctcta gggtcccttc tgg                                             23

<210> SEQ ID NO 19
<211> LENGTH: 34
<212> TYPE: DNA
<213> ORGANISM: Artificial Sequence
<220> FEATURE:
<223> OTHER INFORMATION: primer sequence

<400> SEQUENCE: 19
cagagcccag gatgtccccc agaagggacc ctag                                 34

<210> SEQ ID NO 20
<211> LENGTH: 17
<212> TYPE: DNA
<213> ORGANISM: Artificial Sequence
```

```
<220> FEATURE:
<223> OTHER INFORMATION: primer sequence
<220> FEATURE:
<221> NAME/KEY: modified_base
<222> LOCATION: (14)..(14)
<223> OTHER INFORMATION: wherein t is modified by FAM

<400> SEQUENCE: 20
ccgcagatcc cgcttcg                                                        17

<210> SEQ ID NO 21
<211> LENGTH: 20
<212> TYPE: DNA
<213> ORGANISM: Artificial Sequence
<220> FEATURE:
<223> OTHER INFORMATION: primer sequence
<220> FEATURE:
<221> NAME/KEY: modified_base
<222> LOCATION: (17)..(17)
<223> OTHER INFORMATION: wherein t is modified by ROX

<400> SEQUENCE: 21
gcacttcgct gcagagtacc                                                     20

<210> SEQ ID NO 22
<211> LENGTH: 36
<212> TYPE: DNA
<213> ORGANISM: Artificial Sequence
<220> FEATURE:
<223> OTHER INFORMATION: primer sequence

<400> SEQUENCE: 22
ccgcagatcc cgcttcggta ctctgcagcg aagtgc                                   36

<210> SEQ ID NO 23
<211> LENGTH: 43
<212> TYPE: DNA
<213> ORGANISM: Artificial Sequence
<220> FEATURE:
<223> OTHER INFORMATION: primer sequence

<400> SEQUENCE: 23
gaacacgacc tacgacgagt cagcatctag cttcggacca cca                           43

<210> SEQ ID NO 24
<211> LENGTH: 21
<212> TYPE: DNA
<213> ORGANISM: Artificial Sequence
<220> FEATURE:
<223> OTHER INFORMATION: primer sequence

<400> SEQUENCE: 24
ctgctaccca cagccggtta g                                                   21

<210> SEQ ID NO 25
<211> LENGTH: 21
<212> TYPE: DNA
<213> ORGANISM: Artificial Sequence
<220> FEATURE:
<223> OTHER INFORMATION: primer sequence

<400> SEQUENCE: 25
cacgacctac gacgagtcag c                                                   21

<210> SEQ ID NO 26
<211> LENGTH: 16
<212> TYPE: DNA
```

```
<213> ORGANISM: Artificial Sequence
<220> FEATURE:
<223> OTHER INFORMATION: primer sequence
<220> FEATURE:
<221> NAME/KEY: modified_base
<222> LOCATION: (1)..(1)
<223> OTHER INFORMATION: wherein t is modified by FAM
<220> FEATURE:
<221> NAME/KEY: modified_base
<222> LOCATION: (16)..(16)
<223> OTHER INFORMATION: wherein c is modified by the TaqMan Probe
      MGB-NFQ

<400> SEQUENCE: 26
ttcggaccac cagcac                                                          16

<210> SEQ ID NO 27
<211> LENGTH: 39
<212> TYPE: DNA
<213> ORGANISM: Artificial Sequence
<220> FEATURE:
<223> OTHER INFORMATION: primer sequence

<400> SEQUENCE: 27
gcttcggacc accagcacct aaccggctgt gggtagcag                                 39
```

AMPLIFICATION AND SEQUENCING OF TRANSRENAL NUCLEIC ACIDS

RELATED APPLICATIONS

This application is a continuation of application Ser. No. 13/898,449, filed May 20, 2013, which is a continuation of application Ser. No. 12/505,183, filed Jul. 17, 2009, which claims the benefit of U.S. Provisional Application No. 61/135,364, filed Jul. 18, 2008. The contents of the above priority applications are herein incorporated by reference.

FIELD OF THE INVENTION

The present invention provides highly sensitive methods used for diagnosing and monitoring various diseases and disorders by detecting and analyzing "ultra short" (20-50 base pair) nucleic acids obtained from bodily fluids.

BACKGROUND OF THE INVENTION

Cell death is an essential event in the development and functioning of multicellular organisms, in adult organisms, cell death plays a complementary role to mitosis in the regulation of cell populations. The pathogenesis of numerous diseases involves failure of tissue homeostasis which is presumed to be linked with cytotoxic injury or loss of normal control of cell death.

There exist two major types of cell death, necrosis and apoptosis, marked by different morphological and molecular characteristics (Kerr et al., Br. J. Cancer. 26: 239-257, 1972; Umansky, J. Theor. Biol. 97: 591-602, 1982; Umansky and Tomei, Adv Pharmacol. 41: 383-407, 1997; Ameisen, Cell Death Differ. 11: 4-10, 2004; Lockshin and Zakeri, Int J Biochem Cell Biol. 36: 2405-19, 2004; and Kroemer, et al., Cell Death and Differentiation 12: 1463-1467, 2005). Necrosis is considered to be catastrophic metabolic failure resulting directly from severe molecular and/or structural damage and leads to inflammation and secondary damage to surrounding cells. Apoptosis, also termed programmed cell death, is a much more prevalent biological phenomenon than necrosis and can be induced by specific signals such as hormones, cytokines, by absence of specific signal such as growth or adhesion factors, or by molecular damage that does not cause catastrophic loss of integrity. Apoptosis is a result of an active cellular response involving initiation of an orderly and specific cascade of molecular events. Apoptosis leads to the appearance of distinctive chromatin condensation and margination, nuclear fragmentation, cell shrinkage, and membrane blebbing. Enzymatic internucleosomal fragmentation of nuclear DNA is a hallmark of apoptosis, although some cells die by apoptosis without internucleosomal DNA cleavage (Umansky et al., Biochim Biophys Acta. 655: 9-17, 1981; rends et al., Am J. Pathol. 136: 593-608, 1990; and Zimmermann et al., Pharmacol Ther. 92: 57-70, 2001). Other, more rare forms of cell death, characterized by specific morphology, for example the so-called autophagic cell death, have also been described.

It is well known that apoptosis, or programmed cell death, which is a major form of cell death in multicellular organisms, is accompanied by internucleosomal fragmentation of nuclear DNA. This DNA originates from all cells undergoing apoptosis and thus from all tissues throughout the body. Many laboratories have demonstrated that in humans a portion of this DNA appears in blood (Lo et al., Ann NY Acad Sci. 945: 1-7, 2001; Lichtenstein et al., Ann NY Acad Sci. 945: 239-249, 2001; Taback and Hoon, Curr. Opin Mol Ther. 6: 273-278, 2004; and Bischoff et al., Hum Reprod Update. 8: 493-500, 2002). It has also been shown that this fragmented DNA crosses the kidney barrier (Transrenal DNA or Tr-DNA) and can be detected in the urine (Botezatu et al., Clin Chem. 46:1078-1084, 2000; Su et al., J Mol Diagn. 6:101-107, 2004; and Su et al., Ann NY Acad Sci. 1022: 81-89, 2004).

Both cell-free plasma DNA and Transrenal-DNA (Tr-DNA) have been used as diagnostic tools when the diagnostic marker is the presence of specific, known sequences different from bulk genomic DNA. For example, detection of tumor-specific DNA that results from characteristic mutations can be used for tumor diagnostics, detection of male Y chromosome-specific sequences in urine or blood of a pregnant woman can be used to determine the male gender of the fetus and detection of mutations characteristic of inherited disease can provide a tool for prenatal genetic testing (Chan and Lo, Semin Cancer Biol. 12: 489-496, 2002; Goessl, Expert Rev Mol Diagn. 3: 431-442, 2003; Su et al., J Mol Diagn. 6: 101-107, 2004; Wataganara and Bianchi, Ann NY Acad Sci. 1022: 90-99, 2004; Botezatu et al., Clin Chem. 46: 1078-1084, 2000; and Ding et al., Proc Natl Acad Sci USA. 101: 10762-10767, 2004).

The fate of RNA from dying cells, in particular the mechanisms of its degradation, is much less investigated. However, it is known that fetal RNA can be detected in plasma of pregnant women and RNA with tumor-specific mutations is detectable in plasma of patients with different types of cancer (Tsui et al., Ann NY Acad Sci. 2006; 1075:96-102; Lo and Chiu, Nat Rev Genet. 8: 71-77, 2007; and Tsang and Lo, Pathology 39: 197-207, 2007).

These specific nucleic acid biomarkers are often very short and their concentration in body fluids is usually low, especially if a test addresses an early stage of pregnancy or a disease. Thus, new methods are needed to detect these sensitive biomarkers. The present invention addresses this need in the art.

SUMMARY OF THE INVENTION

The present invention provides a method of detecting non-host nucleic acids originating in areas other than the urinary tract in a patient, including obtaining an urine sample from the patient; and analyzing the urine sample for one or more specific sequences of non-patient nucleic acids that are different from sequences of nucleic acids of the patient and have crossed the kidney barrier wherein the analyzing comprises the step of detecting said one or more specific sequences in the nucleic acids of 20-50 nucleotides in length from the urine sample The present invention also provides a method of detecting nucleic acids of a pathogen, where the nucleic acids originate in areas other than the urinary tract in a patient, including obtaining an urine sample from the patient; and analyzing the urine sample for one or more specific sequences of pathogen nucleic acids that are different from sequences of nucleic acids of the patient and are from pathogen nucleic acids that are 20-50 nucleotides in length and that have crossed the kidney barrier where the analyzing includes the step of detecting the one or more specific sequences from the pathogen.

The present invention also provides a method of detecting cancer in a patient including obtaining an urine sample from the patient; and analyzing the urine sample for one or more specific nucleic acids of 20-50 nucleotides in length, that are indicative of cancer, and that have crossed the kidney barrier, where the analyzing includes the step of detecting the one or more specific nucleic acids indicative of cancer.

The present invention also provides a method of detecting a genetic disease or disorder in a fetus, including obtaining an urine sample from a pregnant female; and analyzing the urine sample for one or more specific fetal nucleic acids of 20-50 nucleotides in length, that have crossed the placental and kidney barriers, where the analyzing includes the step of detecting the one or more specific fetal nucleic acids indicative of a genetic disease.

The present invention also provides a method of monitoring cells, tissues or organs transplanted in areas other than the urinary tract in a patient including obtaining a urine sample from the patient; and analyzing the urine sample for one or more specific sequences of non-patient nucleic acids of 20-50 nucleotides in length from the transplanted cells, tissues or organs that are different from sequences of nucleic acids of the patient and have crossed the kidney barrier to monitor the cells, tissues or organs transplanted in areas other than the urinary tract in the patient. The analyzing step can further include quantitatively analyzing the urine sample for one or more specific sequences of the cell-free, transrenal nucleic acids from dying cells in the transplanted cells, tissues or organs that are different from sequences of nucleic acids of the patient wherein the analyzing comprises the step of detecting said one or more specific sequences of nucleic acids from the transplanted cells, tissues or organs in the nucleic acids that are 20-50 nucleotides in length from urine samples and have crossed the kidney barrier to monitor rejection or acceptance of the transplanted cells, tissues or organs.

The nucleic acids can be DNA or RNA. The pathogen can be a virus, a bacterium, a fungus, a mycoplasma, or a protozoan.

The step of analyzing the urine sample can include hybridization, cycling probe reaction, polymerase chain reaction, nested polymerase chain reaction, PCR to analyze single strand conformation polymorphisms, ligase chain reaction, strand displacement amplification or PCR to analyze restriction fragments length polymorphisms.

The step of analyzing the urine sample can include a polymerase chain reaction that uses primer pairs sufficiently complementary to hybridize with a target sequence of the nucleic acids of interest. Preferably, the target binding sequences for said primer pairs are overlapping or immediately adjacent to each other.

The nucleic acid degradation in the urine sample can be reduced. Reducing the nucleic acid degradation can include inhibiting nuclease activity by increased pH, increased salt concentration, heat inactivation, or by treating said urine sample with a compound selected from the group consisting of: ethylenediaminetetraacetic acid, guanidine-HCl guanidine isothiocyanate, N-lauroylsarcosine, or sodium dodecylsulphate. Preferably, the urine sample has been held in the bladder less than 12 hours.

The step of analyzing the urine sample can further include substantially isolating the nucleic acids of interest in said urine sample. Preferably, the isolation can be by precipitation or using a solid adsorbent material. Preferably, the isolation is by adsorption of the nucleic acids on a resin.

In some embodiments, the methods further comprise filtering the urine sample to remove contaminants. Preferably, the filtering removes nucleic acids comprising more than about 1000 nucleotides or more than about 300 nucleotides.

In some embodiments, the analyzing comprises quantifying said nucleic acids of interest Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In the case of conflict, the present specification, including definitions, will control. In addition, the materials, methods, and examples are illustrative only and not intended to be limiting.

Other features and advantages of the invention will be apparent from the following detailed description and claims.

DETAILED DESCRIPTION OF THE INVENTION

The present invention provides various methods providing a significant increase in sensitivity for analyzing of cell-free, ultra short (20-50 base pairs), nucleic acids obtained from a bodily fluid.

Figure 1:
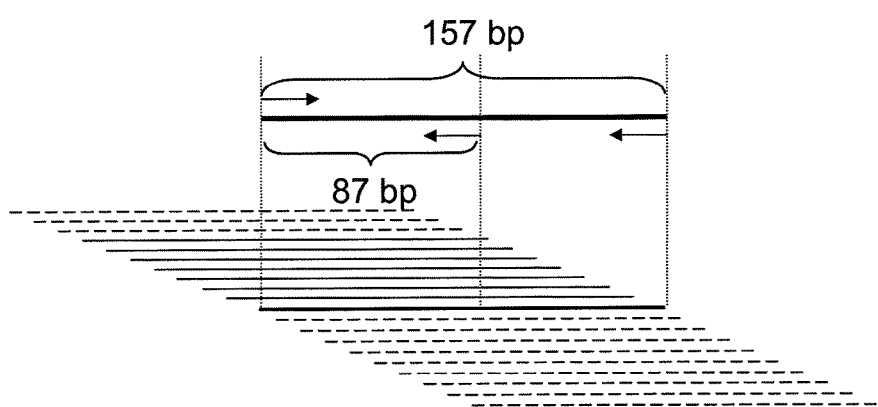
FIG. 1 is a schematic showing the dependence of PCR sensitivity on amplicon size.

Currently, the most sensitive methods for detection of specific DNA or RNA sequences are based on PCR or other amplification techniques. Analysis of cell-free DNA isolated from plasma, urine, and stool by conventional silica-based methods demonstrated that DNA fragments originated from dying fetal or tumor cells are relatively small, around 150 nucleotides (Chan et al., Cancer Res. 63: 2028-2032, 2003; Botezatu et al., Clin Chem. 46:1078-1084, 2000; Su et al., J Mol Diagn. 6: 101-107, 2004; and Diehl et al., Gastroenterology 135: 489-98, 2008). However, it is not always recognized that apoptotic DNA fragmentation is random, and that, consequently, a target sequence of interest is located in DNA fragments that have been cleaved out in a variety of ways. In fact, in any given population of DNA fragments produced by random cleavage the probability of any given target sequence surviving intact to be available for use as PCR template is inversely proportional to the length of such target sequence, as illustrated in FIG. 1. Different lines in FIG. 1 represent short DNA fragments (the 157 base pairs fragments are given as an example) generated by random cleavage of K-RAS in the area of codon 12. Bold solid line represents the only fragment that is amplified by primers designed for the 157-bp amplicon. Thin solid lines represent a subset of DNA fragments amplified by the pair of primers targeting the 87-bp amplicon. Dashed lines are DNA fragments that are not amplified by either set of primers. For example, Su et al., utilize two sets of primers designed for detection of mutant K-RAS (Su, et al., Ann. New York Acad. Sci. 1022: 81-89, 2004).

Most longer targets are out of frame determined by the respective primers. Thus, the advantage of a shorter target size is very significant, especially when target sizes are close to the average fragment length. DNA isolated from urine with a standard silica-based method consists of two fractions, high molecular weight DNA, which originates from shed cells and low molecular weight (150-250 base pair) fraction of Tr-DNA (Botezatu et al., Clin Chem. 46: 1078-1084, 2000; and Su et al., J Mol Diagn. 6: 101-107, 2004).

Furthermore, the application of newly developed technique for isolation of cell-free nucleic acids from body fluids to the isolation of transrenal nucleic acids has revealed the presence in urine of DNA and RNA fragments much shorter than 150 base pairs (U.S. Patent Application Publication No. 20080139801). If these fragments also represent transrenal nucleic acids, amplification of "ultra short" PCR targets or other techniques capable to detect very short nucleic acid sequences with sufficient specificity can significantly increase sensitivity of tests based on analysis of cell-free nucleic acids in urine and other body fluids.

Another reason to aim for "ultra short" targets is the possible presence of single-strand breaks (nicks) in cell-free DNA fragments. In the PCR reaction nucleic acid fragments are used as templates in their single-stranded form, thus further reducing their effective length if cell-free DNA fragments in plasma and Tr-DNA are nicked. These considerations necessitate a PCR assay design capable of detecting exceptionally short target sequences. All considerations discussed above are also applicable any situation when randomly degraded short DNA fragments must be analyzed, e.g. DNA from paraffin-embedded tissues, forensic, or paleontology samples.

Several approaches were used to design primers and probes for detection of ultra short DNA targets by conventional and real time PCR and are described in detail herein. Data obtained with primers/probe sets, designed for detection of ultra short DNA targets (20-50 base pairs), demonstrate: (i) the presence in the urine of DNA and RNA fragments, which are much shorter than those described earlier; (ii) the presence in this low molecular weight nucleic acid fragments of sequences that originated in tissues located outside the urinary system, which means that they have crossed the kidney barrier—transrenal NA (Tr-NA); (iii) much higher sensitivity of Tr-DNA-based tests when ultra short DNA targets are detected compared to conventional PCR target size.

Detection and analysis of ultra short (20-50 base pairs) DNA targets in bodily fluids can significantly increase sensitivity of tests based on analysis of Tr-DNA and cell-free DNA fragments from other bodily fluids. The most commonly used quantitative PCR (qPCR) approach is the Real-Time TaqMan PCR system, which involves the use of 3 target sequence-specific components: 2 primers and 1 labeled TaqMan probe. This standard assay is suitable for amplicons no shorter than about 50 bases, the minimum size being limited by the combined footprint length of the 3 sequence-specific components. There exist a number of alternative qPCR approaches that eliminate the need for a separate TaqMan probe by using various forms of labeled primers, thus allowing for correspondingly shorter targets. However, the elimination of 1 of the 3 sequence-specific components is likely to reduce target specificity of the assay. The present invention addresses target specificity vs. minimum target length by developing novel labeled-primer qPCR assays and modified TaqMan assays. Several new approaches for designing primers or primers/probe sets for detection and quantitative analysis of ultra short sequences by Real-Time PCR are provided. Using these techniques, it has been demonstrated that: (i) analysis of ultra short DNA targets significantly increases sensitivity of the Tr-DNA-based tests; (ii) short DNA fragments (30-150 base pairs) contain human and pathogen Tr-DNA sequences; (iii) larger Tr-DNA fragments are also more effectively detected by primers for ultra short DNA targets, most likely due to the presence of single-strand breaks in those DNA fragments.

The invention relates to a significant increase in sensitivity of tests based on analysis of cell-free nucleic acids obtained from a bodily fluid selected from, but not limited to, the group comprising blood, blood plasma, serum, lymph, interstitial fluid, urine, saliva, sweat, cerebrospinal fluid and others. Preferably, the bodily fluid is obtained non-invasively.

The present invention can be used for many applications, including, but not limited to, analyzing for the presence of pathogen nucleic acids, detecting the presence of nucleic acids indicative of cancer, detecting the presence of nucleic acids indicative of a genetic disease in a fetus, analyzing for the presence of fetal nucleic acids, analyzing for the presence of specific host and specific non-host nucleic acid sequences, for analyzing the form and degree of methylation of a target nucleic acid, detection of single nucleotide polymorphisms and forensic analysis.

The present invention provides methods of detecting nucleic acids of a pathogen, wherein said nucleic acids originate in areas other than the urinary tract in a patient, comprising: (a) obtaining an urine sample from said patient;

and (b) analyzing said urine sample for one or more specific sequences of pathogen nucleic acids that are different from sequences of nucleic acids of the patient and are from pathogen nucleic acids that are 20-50 nucleotides in length and that have crossed the kidney barrier, wherein said analyzing comprises the step of detecting said one or more specific sequences from the pathogen.

A pathogen is a biological agent that can cause disease to its host. A synonym of pathogen is "infectious agent". The term "pathogen" is most often used for agents that disrupt the normal physiology of a multicellular organism.

Infection is the invasion and multiplication of microorganisms in body tissues, which may be clinically unapparent or result in local cellular injury due to competitive metabolism, toxins, intracellular replication or antigen antibody response.

The pathogen nucleic acids can be DNA or RNA. The pathogen is selected from the group consisting of a virus, a bacterium, a fungus, a mycoplasma, and a protozoan.

The methods of the invention are applicable to all viral pathogenic agents, including RNA, DNA, episomal, and integrative viruses. They also apply to recombinant viruses, such as the adenoviruses or lentiviruses utilized in gene therapy. Examples of infectious virus include: Retroviridae (e.g., human immunodeficiency viruses, such as HIV-1, also referred to as HTLV-III, LAV or HTLV-III/LAV, or HIV-111; and other isolates, such as HIV-LP; Picornaviridae (e.g., polio viruses, hepatitis A virus; enteroviruses, human coxsackie viruses, rhinoviruses, echoviruses); Calciviridae (e.g., strains that cause gastroenteritis); Togaviridae (e.g., equine encephalitis viruses, rubella viruses); Flaviridae (e.g., dengue viruses, encephalitis viruses, yellow fever viruses); Coronaviridae (e.g., coronaviruses); Rhabdoviridae (e.g., vesicular stomatitis viruses, rabies viruses); Fidoviridae (e.g., ebola viruses); Paramyxoviridae (e.g., parainfluenza viruses, mumps virus, measles virus, respiratory syncytial virus); Orthomyxoviridae (e.g., influenza viruses); Buiigaviridae (e.g., Hantaan viruses, bunga viruses, phleboviruses and Nairo viruses); Arenaviridae (hemorrhagic fever virus); Reoviridae (e.g., reoviruses, orbiviruses and rotaviruses); Birnaviridae; Hepadnaviridae (Hepatitis B virus); Parvoviridae (parvoviruses); Papovaviridae (papilloma viruses, polyoma viruses); Adenoviridae (most adenoviruses); Herperviridae (herpes simplex virus (HSV) 1 and 2, varicella zoster virus, cytomegalovirus (CMV), herpes viruses); Poxviridae (variola virsues, vaccina viruses, pox viruses); andlridoviridae (e.g., African swine fever virus); and unclassified viruses (e.g., the etiological agents of Spongiform encephalopathies, the agent of delta hepatitides (thought to be a defective satellite of hepatitis B virus), the agents of non-A, non-B hepatitis (class 1-internally transmitted; class 2-parenterally transmitted (i.e., Hepatitis C); Norwalk and related viruses, and astroviruses).

The methods of the invention are applicable to all bacterial pathogenic agents. Examples of infectious bacteria include: *Helicobacter pyloris*, *Borrelia* (e.g., *Borrelia afzelii*, *Borrelia anserine*, *Borrelia burgdorferi*, *Borrelia garinii*, *Borrelia hermsii*, *Borrelia recurrentis*, *Borrelia valaisiana*, and *Borrelia vincentii*); *Rickettsia* (e.g., *Rickettsia felis*, *Rickettsia prowazekii*, *Rickettsia rickettsii*, *Rickettsia typhi*, *Rickettsia conorii*, *Rickettsia africae*, or *Rickettsia akari*); *Legionella pneumophilia*, *Mycobacteria* sps (e.g., *M. tuberculosis*, *M. avium*, *M. Intracellulare*, *M. kansaii M. gordonae*), *Staphylococcus aureus*, *Neisseria gonorrhoeae*, *Neisseria meningitidis*, *Listeria monocytogenes*, *Streptococcus pyogenes* (Group A *Streptococcus*), *Streptococcus agalactiae* (Group B *Streptococcus*), *Streptococcus* (*viridans* group), *Streptococcus faecalis*, *Streptococcus bovis*, *Streptococcus* (*anaerobic* sps.), *Streptococcus pneumoniae*, pathogenic *Campylobacter* sp., *Enterococci* ssp., *Haemophilus influenzae*, *Bacillus antracis*, *corynebacterium diphtheriae*, *corynebacteium* sp., *Erysipelothrix rhusiopathiae*, *Clostridium penfi ingers*, *Clostridium tetani*, *Enterobacter erogenes*, *Klebsiella pneuomiae*, *Pasturella multicoda*, *Bacteroides* sp., *Fusobacterium nucleatum*, *Sreptobacillus moniliformis*, *Treponema pallidium*, *Treponema pertenue*, *Leptospira*, and *Actinomeyces israelli*.

Examples of infectious fungi include: *Cryptococcus neoformans*, *Histoplasma capsulatum*, *Coccidioides immitis*, *Blastomyces dermatitidis*, *Chlamydia trachomatis*, *Candidaalbicans*. Other infectious organisms (i.e., protists) include: *Plasmodium falciparum* and *Toxoplasma gondii*.

In some preferred embodiments, the non-viral pathogen can be *Helicobacter pylori*, *Bacillus anthracis*, *Plasmodium* species or *Leishmania* species.

The step of analyzing for the presence of said pathogen nucleic acid sequence of 20-50 nucleotides in length can be performed using one or more of a variety of techniques, including, but not limited to, hybridization, cycling probe reaction, polymerase chain reaction, nested polymerase chain reaction, polymerase chain reaction-single strand conformation polymorphism, ligase chain reaction, strand displacement amplification and restriction fragments length polymorphism. Preferably, the analysis step also includes FRET-dependent fluorescence detection. Preferably, the step of performing the polymerase chain reaction can comprise using primers with binding sites which are either immediately adjacent to each other on the target sequence or slightly overlapping (having no intervening sequences between the primer binding sites).

The present invention further encompasses methods having the step of reducing DNA degradation in said urine sample, which in one embodiment encompasses treatment with a compound selected from the group comprising: ethylenediaminetetraacetic acid, guanidine-HCl, guanidine isothiocyanate, N-lauroylsarcosine, and Na-dodecylsulphate. DNA degradation can further be reduced by taking a urine sample that has been held in the bladder less than 12 hours.

In one embodiment, it is beneficial to substantially isolate said nucleic acid sequence prior to assaying the urine for the presence of a pathogen nucleic acid sequence, that has crossed the kidney barrier. In alternate embodiments, the nucleic acid sequence is substantially isolated by precipitation or by treatment with a solid adsorbent material. In another embodiment, the urine sample is filtered to remove contaminants, and, in a specific embodiment, the filtering removes DNA comprising more than about 1000 nucleotides. Preferably, the filtering removes DNA comprising more than about 300 nucleotides.

Further encompassed by the present invention is a diagnostic kit for detecting pathogen in the urine, comprising: reagents to facilitate the isolation of DNA of 20-50 nucleotides in length from urine; reagents to facilitate amplification of DNA of 20-50 nucleotides in length by the polymerase chain reaction; a heat stable DNA polymerase; and an oligodeoxynucleotide specific for a pathogen nucleic acid sequence.

The present invention provides methods of detecting cancer in a patient, comprising: providing a urine sample from a patient; and analyzing said urine sample for a nucleic acid sequence of 20-50 nucleotides in length, indicative of cancer, that has crossed the kidney barrier.

In one embodiment, analyzing for the presence of said nucleic acid sequence comprises amplifying said nucleic acid sequence indicative of cancer. In another specific embodiment, said analyzing comprises quantifying the number of copies of said nucleic acid sequence. In one embodiment said nucleic acid sequence contains an anomaly indicative of colon cancer. In another embodiment, said nucleic acid sequence contains mutant K-ras DNA.

Cancer includes solid tumors, as well as, hematologic tumors and/or malignancies. Various cancers to be treated include but are not limited to breast cancer, lung cancer, colorectal cancer, pancreatic cancer, ovarian cancer, prostate cancer, renal carcinoma, hepatoma, brain cancer, melanoma, multiple myeloma, lymphoma, Hodgkin's lymphoma, non-Hodgkin's lymphoma, childhood lymphomas, and lymphomas of lymphocytic and cutaneous origin, leukemia, childhood leukemia, hairy-cell leukemia, acute lymphocytic leukemia, acute myelocytic leukemia, chronic lymphocytic leukemia, chronic myelocytic leukemia, chronic myelogenous leukemia, and mast cell leukemia, myeloid neoplasms, mast cell neoplasms, hematologic tumor, and lymphoid tumor, including metastatic lesions in other tissues or organs distant from the primary tumor site. Cancers to be treated include but are not limited to sarcoma, carcinoma, and adenocarcinoma.

The step of analyzing for the presence of said nucleic acid sequence of 20-50 nucleotides in length can be performed using one or more of a variety of techniques, including, but not limited to, hybridization, cycling probe reaction, polymerase chain reaction, nested polymerase chain reaction, polymerase chain reaction-single strand conformation polymorphism, ligase chain reaction, strand displacement amplification and restriction fragments length polymorphism. Preferably, the analysis step also includes FRET-dependent fluorescence detection. Preferably, the step of performing the polymerase chain reaction can comprise using primers with binding sites which are either immediately adjacent to each other on the target sequence or slightly overlapping (having no intervening sequences between the primer binding sites).

The present invention further encompasses methods having the step of reducing DNA degradation in said urine sample, which in one embodiment encompasses treatment with a compound selected from the group comprising: ethylenediaminetetraacetic acid, guanidine-HCl, Guanidine isothiocyanate, N-lauroylsarcosine, and Na-dodecylsulphate. DNA degradation can further be reduced by taking a urine sample that has been held in the bladder less than 12 hours.

In one embodiment, it is beneficial to substantially isolate said nucleic acid sequence prior to assaying the urine for the presence of a nucleic acid sequence, indicative of cancer, that has crossed the kidney barrier. In alternate embodiments, the nucleic acid sequence is substantially isolated by precipitation or by treatment with a solid adsorbent material. In another embodiment, the urine sample is filtered to remove contaminants, and, in a specific embodiment, the filtering removes DNA comprising more than about 1000 nucleotides. Preferably, the filtering removes DNA comprising more than about 300 nucleotides.

In yet another embodiment, a method of monitoring cancer treatment in a patient is encompassed, comprising: providing a urine sample from a patient; and analyzing said urine sample for the quantity of a nucleic acid sequence of 20-50 nucleotides in length, indicative of cancer, that has crossed the kidney barrier.

Further encompassed by the present invention is a diagnostic kit for detecting a genetic mutation indicative of cancer in the DNA of a patient, comprising: reagents to facilitate the isolation of DNA of 20-50 nucleotides in length from urine; reagents to facilitate amplification of DNA of 20-50 nucleotides in length by the polymerase chain reaction; a heat stable DNA polymerase; and an oligodeoxynucleotide specific for a sequence only occurring in a genetic mutation characteristic of cancer.

The present invention provides methods of analyzing a fragment of fetal DNA of 20-50 nucleotides in length that has crossed the placental and kidney barriers, comprising: obtaining a urine sample, suspected of containing fetal polymeric transrenal nucleic acids, from a pregnant female; and assaying for the presence of said fetal polymeric DNA of 20-50 nucleotides in length in said urine sample.

In one embodiment of the present invention, the presence of the particular unique fetal DNA of 20-50 nucleotides in length sequence is indicative of a genetic disease.

The target fetal DNA sequence can be, for example, a sequence that is present only on the Y chromosome. The step of assaying for the presence of unique fetal DNA sequence of 20-50 nucleotides in length can be performed using one or more of a variety of techniques, including, but not limited to, hybridization, cycling probe reaction, cleavage product detection, polymerase chain reaction, nested polymerase chain reaction, polymerase chain reaction-single strand conformation polymorphism, ligase chain reaction, strand displacement amplification and restriction fragments length polymorphism. Preferably, the analysis step also includes FRET-dependent fluorescence detection. The step of performing the polymerase chain reaction can comprise using primers substantially complementary to a portion of the unique fetal DNA sequence, and the unique fetal DNA sequence can be a sequence that is present in the paternal genome and not present in the maternal genome. Preferably, the step of performing the polymerase chain reaction can comprise using primers with binding sites which are either immediately adjacent to each other on the target sequence or slightly overlapping (having no intervening sequences between the primer binding sites).

The present invention further encompasses methods having the step of reducing DNA degradation in the urine sample. Reducing DNA degradation can be by treatment with compounds selected from the group consisting of: ethylenediaminetetraacetic acid, guanidine-HCl, Guanidine isothiocyanate, N-lauroylsarcosine, and Na-dodecylsuiphate. DNA degradation can further be reduced by taking a urine sample that has been held in the bladder less than 12 hours.

The present invention encompasses methods where DNA in the urine sample is substantially isolated prior to assaying for the presence of a unique fetal DNA sequence in the urine sample. Substantial isolation can be by, but is not limited to, precipitation and adsorption on a resin.

In some cases, it can be desirable to filter the urine sample to remove contaminating nucleic acids before assaying. In a specific embodiment, the filtering removes DNA comprising more than about 1000 nucleotides. Preferably, the filtering removes DNA comprising more than about 300 nucleotides.

The present invention further encompasses a method of determining the sex of a fetus, comprising: obtaining a urine sample, suspected of containing fetal male DNA of 20-50 nucleotides in length, from a pregnant female; amplifying a portion of the male DNA of 20-50 nucleotides in length present in the urine sample by the polymerase chain reaction, using an oligodeoxynucleotide primer having sequences specific to a portion of the Y chromosome, to produce amplified DNA; and detecting the presence of the amplified DNA.

The present invention also encompasses a diagnostic kit for detecting the presence of human male fetal DNA of 20-50 nucleotides in length in maternal urine, comprising: reagents to facilitate the isolation of DNA from urine; reagents to facilitate amplification of DNA by the polymerase chain reaction; a heat stable DNA polymerase; and an oligodeoxynucleotide specific for a sequence only occurring on the Y chromosome.

The present invention also encompasses methods of analyzing a target nucleic acid sequence of 20-50 nucleotides in length in urine, comprising: providing a urine sample; and assaying the urine sample for the presence of a target nucleic acid sequence of 20-50 nucleotides in length that has crossed the kidney barrier.

In one embodiment, the target nucleic acid sequence of 20-50 nucleotides in length comprises an altered gene sequence, and that altered gene sequence can comprise a modification occurring in tumor cells in specific. The target nucleic acid sequence of 20-50 nucleotides in length can be a host nucleic acid or a non-host nucleic acid.

The target nucleic acid can also be a single nucleotide polymorphism (SNP), which is a DNA sequence variation occurring when a single nucleotide in the genome (or other shared sequence) differs between members of a species (or between paired chromosomes in an individual). The nucleic acid sequence comprising the SNP can be any length. Preferably, the nucleic acid sequence comprising the SNP is less than 50 nucleotides. More preferably, the nucleic acid sequence comprising the SNP is between 20-50 nucleotides in length. The nucleic acid sequence comprising the SNP can be a host nucleic acid or a non-host nucleic acid.

The present invention also encompasses methods of analyzing a target nucleic acid sequence of 20-50 nucleotides in length in any bodily fluid or tissue to perform forensic analysis, comprising: providing a fluid or tissue sample; and assaying the fluid or tissue sample for the presence of a target nucleic acid sequence of 20-50 nucleotides in length that has crossed the kidney barrier. The method can further comprise quantitative analysis of said target nucleic acid sequence. Preferably, the method can further comprise the sequencing of said target nucleic acid sequence using any method known in the art.

The step of assaying for the presence of a target DNA sequence can be selected from the group consisting of hybridization, cycling probe reaction, polymerase chain reaction, nested polymerase chain reaction, polymerase chain reaction-single strand conformation polymorphism, ligase chain reaction, strand displacement amplification and restriction fragments length polymorphism. The step of assaying for the presence of a target DNA sequence can comprise techniques for amplifying the target DNA. Preferably, the analysis step also includes FRET-dependent fluorescence detection. Preferably, the step of performing the polymerase chain reaction can comprise using primers with binding sites which are either immediately adjacent to each other on the target sequence or slightly overlapping (having no intervening sequences between the primer binding sites).

The present invention further encompasses methods having the step of reducing DNA degradation in the urine sample prior to assaying the urine sample for the presence of a target DNA sequence that has crossed the kidney barrier. Reducing DNA degradation can be by treatment with compounds selected from the group consisting of: ethylenediaminetetraacetic acid, guanidine-HCl, Guanidine isothiocyanate, N-lauroylsarcosine, and Na-dodecylsulphate. DNA degradation can further be reduced by taking a urine sample that has been held in the bladder less than 12 hours.

The present invention encompasses methods where DNA in the urine sample is substantially isolated prior to assaying for the presence of a target DNA sequence that has crossed the kidney barrier. Substantial isolation can be by, but is not limited to, precipitation and adsorption on a resin. In some cases, it is desirable to filter the urine sample to remove contaminating nucleic acids before assaying for the presence of a target DNA sequence that has crossed the kidney barrier. In a specific embodiment, the filtering removes DNA comprising more than about 1000 nucleotides. Preferably, the filtering removes DNA comprising more than about 300 nucleotides.

The present invention also encompasses methods of analyzing a target nucleic acid sequence in urine, comprising: providing a urine sample, suspected of containing DNA that has crossed the kidney barrier, from a patient; amplifying a target DNA sequence in the DNA that has crossed the kidney barrier, comprising using a primer substantially complementary to a portion of the target DNA sequence that does not occur in cells of the urinary tract of the patient, to make amplified target DNA; and detecting the presence of the amplified target DNA. Amplification can comprise performing a polymerase chain reaction. The target DNA sequence can comprise an altered gene sequence, such as a modification occurring in tumor cells.

The present invention provides methods of monitoring transplanted material in a patient, comprising: providing a urine sample suspected of containing nucleic acid from transplanted material; and analyzing said urine sample for a nucleic acid sequence of 20-50 nucleotides in length that has crossed the kidney barrier and that was not present in the patient prior to transplantation. In a specific embodiment, the nucleic acid sequence of 20-50 nucleotides in length is not present in cells of the urinary tract of said patient.

In a specific embodiment, the analyzing comprises amplifying said nucleic acid sequence of 20-50 nucleotides in length with a primer substantially complementary to a part of said nucleic acid sequence that does not occur in cells of the urinary tract of the patient, to make amplified target DNA, and detecting the presence of said amplified target DNA. More specifically, the amplifying can comprise performing a polymerase chain reaction. Preferably, the analysis step also includes FRET-dependent fluorescence detection. Preferably, the step of performing the polymerase chain reaction can comprise using primers with binding sites which are either immediately adjacent to each other on the target sequence or slightly overlapping (having no intervening sequences between the primer binding sites).

In another specific embodiment is included the additional step of reducing DNA degradation in said urine sample, which can be performed in any way known, but, without limitation, includes situations wherein reducing DNA degradation is by treatment with a compound selected from the group consisting of: ethylenediaminetetraacetic acid, guanidine-HCl, Guanidine isothiocyanate, N-lauroylsarcosine, and Na-dodecylsulphate. DNA degradation can further be reduced by taking a urine sample that has been held in the bladder less than 12 hours.

It is desirable in some embodiments to substantially isolate said nucleic acid sequence. In alternate embodiments, the nucleic acid sequence is substantially isolated by precipitation, and/or by adsorption on a resin. Additionally, one can filter the urine sample to remove contaminants. In a specific embodiment, this filtering removes DNA comprising more than about 1000 nucleotides.

Further encompassed by the present invention is a diagnostic kit for detecting DNA from a transplanted material in the urine of a patient, comprising: reagents to facilitate the isolation of DNA of 20-50 nucleotides in length from urine; reagents to facilitate amplification of DNA of 20-50 nucleotides in length by the polymerase chain reaction; a heat stable DNA polymerase; and an oligodeoxynucleotide specific for a sequence that occurs in the transplanted material, and did not occur in the patient prior to transplantation.

The present invention provides methods of analyzing for the presence of specific fetal ultra short nucleic acid sequences or ultra short nucleic acid modifications by detecting specific fetal nucleic acid sequences in bodily fluids. Preferably, the nucleic acid sequences have crossed the placental and kidney barriers and are present in maternal urine. The methods generally involve the steps of obtaining a urine sample from a pregnant woman and subjecting the material to a method of detecting a specific fetal ultra short nucleic acid sequence or modification of interest. In one embodiment, the method further encompasses substantially purifying nucleic acids present in the urine sample prior to detecting the specific ultra short nucleic acid sequence or modification of interest. These methods have a variety of diagnostic applications, including the determination of fetus sex and the identification of fetal genetic diseases, such as those inherited from the father for various purposes, including determinations of paternity.

The inventions described herein can be used, for example, to diagnose any of the more than 3000 genetic diseases currently known or to be identified (e.g. hemophilias, thalassemias, Duchenne muscular dystrophy, Huntington's disease, Alzheimer's disease and cystic fibrosis). Any genetic disease for which the mutation(s) or other modification(s) and the surrounding nucleotide sequence is known can be identified by methods of the present invention. Some diseases may be linked to known variations in methylation of nucleic acids, that can also be identified by methods of the present invention.

Further, there is growing evidence that some DNA sequences can predispose an individual to any of a number of diseases such as diabetes, arteriosclerosis, obesity, various autoimmune diseases and cancer (e.g. colorectal, breast, ovarian, lung), or chromosomal abnormality (either prenatally or postnatally). The diagnosis for a genetic disease, chromosomal aneuploidy or genetic predisposition can be performed prenatally by collecting an appropriate bodily fluid, such as, urine from the pregnant mother.

Ultra short DNA analysis obtained non-invasively from a bodily fluid provides an easier and safer way to perform prenatal testing. Preferably, the bodily fluid is urine. A fetus receives equal amount of genetic information from both parents. The loss of a large number of fetal cells during development is a major part of the genetic program for embryonic differentiations and formation of a normal body. DNA from these dying embryonic cells not only escapes into the bloodstream of the mother, but also crosses the kidney barriers where it appears in the mother's urine. Pieces of the male-specific Y chromosome have been found in the urine of women pregnant with male fetuses. Fetal genetic information was found in the mother's urine as early as the $7^{th}$ to $8^{th}$ week of pregnancy, that is, at least 6-8 weeks earlier than can be obtained by either amniocentesis or chorionic villus sampling. See, for Example U.S. Pat. No. RE39,920.

In one embodiment of this invention, a simple noninvasive test can be used for early determination of the fetal gender. However, there are more far-reaching consequences of these findings with regard to development of modern safe diagnostic techniques. The discovery that ultra short DNA from the developing embryo appears in the mother's urine presents the opportunity to quickly develop products for analysis of genes inherited from the father. These include genes that contain disease-related mutations or can cause problems on different genetic backgrounds. As an example, if a pregnant woman is Rh-(negative Rhesus factor) and produces anti-RhD antibodies and a father is $Rh^+$, amniocentesis is currently recommended for early diagnostics of Rh incompatibility, which often causes life threatening hemolytic anemia in the newborn baby. Detection of the RhD gene-specific sequence in the mother's urine will be an excellent alternative to amniocentesis, which is considered hazardous by a growing number of physicians worldwide. This test is also less expensive and more cost-effective, because it avoids the necessity of a surgical step in obtaining samples for analysis.

With the advent of broad-based genetic mapping initiatives such as the Human Genome Project, there is an expanding list of targets and applications for genetic analysis of urine ultra short DNA. Many diseases inherited by the fetus will be easily detectable by analysis of the mother's urine DNA. These include Marfan Syndrome, Sickle Cell Anemia, Tay Sachs Disease, and a group of neurodegenerative disorders, including Huntington's Disease, Spinocerebellar Ataxia 1, Machado-Joseph Disease, Dentatorubraopallidoluysian Atrophy, and others that affect the fetus and newborn. Urine DNA analysis can detect the presence of the mutant gene inherited from the father. Also, if the mother's genome bears a mutation, the test can help determine whether a normal version of the gene has been inherited from the father.

In addition to providing answers to commonly asked questions from expectant couples, determination of fetal sex can also be very helpful if there is a risk of X chromosome-linked inherited disease, e.g. Hemophilia or Duchenne Muscular Dystrophy. Again prenatal testing for inherited diseases is currently performed with specimens obtained by amniocentesis. There are two major disadvantages of this technology: First, amniocentesis can only be performed after the $14^{th}$ week of pregnancy. Second, in some instances, the risk associated with an inherited disorder is comparable to the risk associated with the surgical procedure of amniocentesis. Urine DNA based technology can present the information while avoiding both problems.

The methods of the present invention provide a significant increase in sensitivity for analyzing fetal, cell-free, ultra short (20-50 base pairs), nucleic acids Another important factor contributing to the success of any new diagnostic test is the necessity that patients and doctors express a preference for the new test. Invasive prenatal testing is often declined by the patient because of the attendant risks to the fetus and mother. If the same information can be obtained from a safe and simple urine test, it is likely that the test will be given widespread acceptance by the public and medical community.

The present invention further provides methods enabling the detection of specific ultra short nucleic acid sequences originating from the patient's own endogenous nucleic acid. These ultra short nucleic acid sequences are obtained non-invasively from a bodily fluid. Preferably, the nucleic acids sequences must cross the kidney barrier to appear in the urine. The method generally involves the steps of obtaining a urine sample from a patient and subjecting the material to a method of detecting a target nucleic acid sequence. In one embodiment, the method further encompasses substantially purifying nucleic acids present in the urine sample prior to detecting the target nucleic acid. This method has a variety of diagnostic applications, including, but not limited to, tumor diagnosis and the diagnosis of diseases caused by clonal expansion of cells containing DNA modifications accompanied by death of at least a subset of the cells bearing DNA modifications.

Success of tumor treatment is currently dependent on tumor type and method of treatment. However, the most important factor determining the success of cancer therapy is detection of the tumor at the earliest possible stage of development. The earlier a tumor is detected the better is the prognosis. In many per-neoplastic conditions, such as inherited predisposition to a specific tumor type or a disease promoting neoplastic transformation, (e.g. chronic hepatitis and cirrhosis), significant efforts for early tumor detection are currently being applied but existing techniques are usually invasive and expensive. The oncologist's arsenal now includes tests that are not only invasive, often hazardous, but also less reliable than expected.

From the patient's point of view, the invasive tests are expensive and sufficiently unpleasant to warrant decisions to forgo needed tests such as rectocolonoscopy for diagnostics of colorectal cancer. The problem of compliance is of critical importance when high-risk patients are encouraged to submit to procedures that are clearly uncomfortable and unpleasant. Dramatic improvement of high-risk patient compliance is an absolute necessity for the future. Thus, development of new methods for early tumor detection is absolutely necessary for a substantial progress in this area of medicine. It is also clear that such methods should be based not only on more sensitive techniques for detection of clinical symptoms of neoplastic growth, but rather on revealing tumor cell-specific markers.

The methods of the present invention provide a significant increase in sensitivity for analyzing cell-free, ultra short (20-50 base pairs), nucleic acids originating from the patient's or subject's own endogenous nucleic acid.

The earliest cellular changes that can be used as a marker of neoplastic transformation are changes that cause the transformation, i.e. genetic and epigenetic DNA modification. Various changes in DNA sequences and/or in the methylation status of CpG islands (especially of those located in promoter regions of tumor suppressor genes) are currently used as tumor markers. As more such markers are discovered, it has become evident that some are characteristic of early tumor stages, or even of pre-neoplastic conditions. Other DNA modifications can indicate relatively late phases of neoplastic transformation. Also there are expectations that some changes in DNA sequences and its methylation pattern will help predict metastatic potential and tumor cell sensitivity to different chemotherapeutic agents. Cell death occurs at all stages of tumor growth and detection of tumor-specific changes in the urine DNA can be an excellent marker for tumor diagnosis and monitoring of anti-tumor therapy. A tumor-specific mutation of the K-ras gene can be detected in the urine of patients with colorectal tumors that bear this mutation.

One of the greatest clinical challenges for tumor chemotherapy is the variable sensitivity of different tumors to anti-tumor drugs, and the absence of a simple test for the quick early stage evaluation of anti-tumor therapy. Normally, the oncologist can observe the results of treatment only after several months. Meanwhile, the tumor can continue to grow and possibly metastasize if the chemotherapeutic regimen is ineffective. One embodiment of the present invention, useful for the immediate monitoring of the effectiveness of tumor therapy, is the quantitative analysis of tumor-specific mutations in the patient's urine DNA. If the treatment is effective, then more tumor cells die, and the ratio of the mutant sequence to any normal reference sequence contained in the urine will increase. Eventually, if chemotherapy is effective the mutant tumor-specific sequence will disappear. Periodic analysis of a patient's urine DNA can be used for monitoring of possible tumor re-growth. Early indication of chemotherapeutic ineffectiveness would allow time to try other chemotherapeutics and anti-tumor treatments. This approach is similarly effective for the evaluation of the effectiveness of radiation therapy and other cancer therapies and for monitoring after surgical treatment of cancerous growths.

The present invention also provides methods enabling the detection of specific ultra short nucleic acid sequences that do not originate from the patient's endogenous nucleic acid sequences. These ultra short nucleic acid sequences are obtained non-invasively from a bodily fluid. Preferably, the nucleic acid sequences must cross the kidney barrier to appear in the urine. The steps are the same as for the detection of host originated nucleic acids, except that the detection method selects for non-host nucleic acid sequences. This method has a variety of diagnostic applications, including, but not limited to, diagnosis of infection by nucleic acid containing pathogens that infect areas other than the urinary tract, and do not shed nucleic acids directly into the urinary tract.

The methods of the present invention provide a significant increase in sensitivity for analyzing cell-free, ultra short (20-50 base pairs), nucleic acids that do not originate from the patient's or subject's own endogenous nucleic acid.

In one embodiment, the present invention has important applications in organ and tissue transplanting science. Transplantation of different organs, tissues, and cells or other material that contains nucleic acids (referred to as "transplanted material") is now widely used in clinical practice. The most important problem faced by the transplant patient and the healthcare delivery system is the requirement to carefully control the normal immune response of the recipient that leads to transplant rejection and failure. In spite of intensive therapy designed to suppress the recipient's immune response, rejection episodes often occur during the post-transplantation period and their early detection can be very useful, if not critical for effective clinical management.

Each person has a distinct and unique pattern of genes that are encoded by DNA. Since the donor's DNA is genetically different from the recipient's DNA, the present invention can be used to "monitor transplanted material" which is defined as detecting and/or measuring the rejection or acceptance of transplanted organs, tissues and cells by the recipient. This will reduce and even eliminate in some instances the necessity of taking tissue biopsies from already debilitated patients. A test for the appearance of Y chromosome-specific DNA sequences in the urine of female recipients who had received blood transfusions with blood from males has been described. See, for Example U.S. Pat. No. RE39,920. These experiments showed that due to the death of white blood cells from the male donor, Y chromosome-specific sequences appeared in the urine of the female recipient. These blood cells die in such the same manner as the cells of a transplanted organ that has been attacked by the recipient's immune system. Methods of the present invention can be used to track the progress of recipients of cell, tissue and organ transplants.

Changes in DNA methylation of specific genomic areas affect chromatin structure and DNA transcription, and consequently, are being investigated for their involvement in various pathological processes. As such, analysis of ultra short transrenal DNA methylation is a useful diagnostic tool.

Mutations and changes in DNA methylation status that happen during tumor progression can be used as the tumor markers (Esteller et al., Cancer Res 59:67-70, 1999; Wong et al., Cancer Res 59: 71-3, 1999). Various changes in DNA sequences and/or in the methylation status of CpG islands (especially of those located in promoter regions of tumor suppressor genes) are currently used as tumor markers (Baylin et al., Adv Canc Res 72:141-96, 1998). Also there are expectations that some changes in DNA sequences and its methylation pattern will help to predict metastatic potential and tumor cell sensitivity to different chemotherapeutic agents. methylation in CpG islands of some genes, e.g. MYF-3 gene, can be bound to different stages of carcinogenesis. Hypermethylation of this gene in comparison with normla mucosa was observed in 88% of adenomas and 99% of carcinomas (Shannon et al., Int J Cancer 84:109-13, 1999).

There are no reliable markers based on DNA mutations for HCC. However, in this case there is a growing group of markers that are based on CpG island methylation in a gene promoter region, e.g. the p16 or GSTPI promoter. p16 methylation was found in more than 70% of HCC tissues and among HCC cases with aberrant methylation similar changes were also detected in about 80% of the plasma samples (Wong et al., Cancer Res 59:71-3, 1999; Matsuda et al., Gastroenterology 116:394-400, 1999). Somatic hypermethylation of GSTP1 CpG islands was observed in DNA from more than 80% of HCC cases (Tchou et al., Int J Oncol 16:663-76, 2000)

Methylation of CpG islands in promoters of tumor suppressor genes lead to their inactivation and are involved in pre-neoplastic conditions and carcinogenesis, and, as such, can be used for diagnostics of those pathological processes. Methylation of estrogen-receptor gene has been linked to heart disease (Fricker J., Mol. Med. Today, 5, 505-506, 1999). Fragile X chromosome syndrome is associated not only with the expansion of the number of CGG trinucleotide tandem repeats at the 5' untranslated region of the FMR1 gene but also with hypermethylation in the CGG repeats and the adjacent CpG islands (Panagopoulos et al., Hum. Mutat., 14, 71-79, 1999). Analysis of the methylation status at the CpG islands of the small nuclear ribonucleoprotein associated polypeptide N (SNRPN) gene using amniotic fluid cell cultures or cultivated chorionic vilus samples has been recommended for prenatal diagnosis of Prader-Willi and Angelman syndromes (Kubota et al., J. Med. Genet., 33, 1011-1014, 1996). DNA hypermethylation of the promoter region of the E-cadherin gene is characteristic of chronic hepatitis and liver cirrhosis (Kanai et al., Cancer Lett., 148, 73-80, 2000). Of course many more modifications in DNA methylation status will be linked to various disease in the future. Detection of those modifications in transrenal DNA will be a useful marker in prenatal testing as well as for diagnosis of pathological processes in adult organisms.

It is also known that aging is accompanied by specific changes in the genome methylation status, hypermethylation of some CpG islands and demethylation in coding regions of genome (Toyota and Issa, Seminars in Cancer Biol., 9, 349-357, 1998). Detection of these changes in transrenal DNA, that contains DNA fragments from various cell types, can be used as a marker of normal and pathological aging processes.

Techniques for nucleic acid manipulation useful for the practice of the present invention are described in a variety of references, including but not limited to, Molecular Cloning: A Laboratory Manual, 2nd ed., Vol. 1-3, eds. Sambrook et al. Cold Spring Harbor Laboratory Press (1989); and Current Protocols in Molecular Biology, eds. Ausubel et al., Greene Publishing and Wiley-Interscience: New York (1987) and periodic updates. Specific descriptions, while not intended to limit the scope of the present invention, provide guidance in practicing certain aspects of the present invention.

DNA is subject to degradation by DNases present in bodily fluids, such as urine. The present invention encompasses several methods for preventing or reducing the degradation of DNA while in urine so that sufficiently large sequences are available for detection by known methods of DNA detection such as those described below. In one embodiment, samples of urine are taken when the urine has been held in the bladder for less than 12 hours, in a specific embodiment the urine is held in the bladder for less than 5 hours, more preferable for less than 2 hours. Collecting and analyzing a urine sample before it has been held in the bladder for a long period of time reduces the exposure of DNA to the any DNase present in the urine.

In another embodiment of the present invention, after collection, the urine sample is treated using one or more methods of inhibiting DNase activity. Methods of inhibiting DNase activity include, but are not limited to, the use of ethylenediaminetetraacetic acid (EDTA), guanidine-HCl, GITC (Guanidine isothiocyanate), N-lauroylsarcosine, Na-dodecylsulphate (SDS), high salt concentration and heat inactivation of DNase.

In yet another embodiment, after collection, the urine sample is treated with an adsorbent that traps DNA, after which the adsorbent is removed from the sample, rinsed and treated to release the trapped DNA for detection and analysis. This method not only isolates DNA from the urine sample, but, when used with some adsorbents, including, but not limited to Hybond N membranes (Amersham Pharmacia Biotech Ltd., Piscataway, N.J.) protects the DNA from degradation by DNase activity.

In some cases, the amount of DNA in a urine sample is limited. Therefore, for certain applications, the present invention encompasses embodiments wherein sensitivity of detection is increased by any method(s) known in the art, including, without limitation, one or more of the following methods.

Where DNA is present in minute amounts in the urine, larger urine samples can be collected and thereafter concentrated by any means that does not effect the detection of DNA present in the sample. Some examples include, without limiting the breadth of the invention, reducing liquid present in the sample by butanol concentration or concentration using Sephadex G-25 (Pharmacia Biotech, Inc., Piscataway N.J.).

Nested PCR can be used to improve sensitivity by several orders of magnitude. Because of the vulnerability of nested PCR to inaccurate results due to DNA contamination, in one embodiment of the present invention, precautions are taken to avoid DNA contamination of the sample. For example, without limiting the present invention, one can treat PCR reagents with restriction endonuclease(s) that cleave within the target sequence, prior to adding them to the test DNA sample.

In one embodiment, the present invention encompasses substantially purifying or isolating nucleic acids from a sample prior to detection. Nucleic acid molecules can be isolated from urine using any of a number of procedures, which are well-known in the art. Any method for isolation that facilitates the detection of target nucleic acid is acceptable. For example, DNA can be isolated by precipitation, as described by Ishizawa et al., Nucleic Acids Res. 19, 5972 (1991). Where a large volume sample contains a low concentration of DNA, as with urine, a preferred method of isolating DNA is encompassed. In this method, a sample is treated with an adsorbent that acts to concentrate the DNA. For example, a sample can be treated with a solid material that will adsorb DNA, such as, without limitation, DEAE Sephadex A-25 (Pharmacia Biotech, Inc., Piscataway N.J.), a DNA filter, and/or glass milk. Sample DNA is eluted from the adsorbent after other compositions are washed away.

In consideration of the sensitivity of various nucleic acid analyzing techniques, such as PCR, the present invention also encompasses methods of reducing the presence of contaminating nucleic acids in the urine sample. Contamination of urine samples by nucleic acid sequences that have not crossed the kidney barrier can be introduced by cells shedding from the urinary tract lining, by sexual intercourse, or during processing of the urine sample prior to detection of the DNA sequence of interest. Without intending to limit the present invention to any mechanism, it is believed that DNA passing the kidney barrier and appearing in urine is likely to have on average a shorter length than DNA introduced from contaminating sources because of the fragmentation that occurs in apoptotic cells and necrotic cells in the body, combined with the action of DNase in the blood and urine.

Filtration can be used to reduce the level of contaminating DNA in a urine sample prior to detection, by selecting for shorter sequences of DNA. In one embodiment of the present invention nucleic acids containing more than about 1000 base pairs, or 1000 nucleotides when denatured, are removed from the sample prior to detection. In a specific embodiment of the present invention, urine samples are filtered prior to amplification by PCR to remove substantially all DNA comprising greater than 300 base pairs, or 300 nucleotides when denatured. Without limiting the invention to a specific mechanism, it is proposed that such a filtration removes contaminating DNA from cells shed from the urethral/bladder wall or introduced into the urethra during sexual intercourse. The majority of DNA from such contaminating sources are likely to comprise more than 300 nucleotides as the DNA is not for the most part a product of fragmentation of nucleic acids as a result of apoptotic cell death.

Nucleic acid molecules can also be isolated by gel electrophoresis, whereby fragments of nucleic acid are separated according to molecular weight. The technique of restriction fragments length polymorphisms (RFLP), applies the methods of electrophoresis separation, followed by nucleic acid detection enabling comparison by molecular weight of fragments from two or more alleles of a specific gene sequence.

The above-mentioned methods of purification are meant to describe, but not limit, the methods suitable for use in the invention. The methods of isolating nucleic acids are within the ability of one skilled in the art and are not described in detail here.

The expression "assaying for the presence of a nucleic acid sequence" refers to the use of any method to determine whether or not a nucleic acid sequence is present in a sample. Methods include, but are not limited to, techniques for hybridization, amplification and detection of nucleic acids. One skilled in the art has access to a multitude of these methods, including, but not limited to, those set forth in Current Protocols in Molecular Biology, eds. Ausubel et al., Greene Publishing and Wiley-Interscience: New York (1987) and periodic updates. It is contemplated that two or more methods can be used in combination to confirm the results or improve the sensitivity of the assay. An example of analyzing by the combination of methods to determine whether or not a nucleic acid sequence is present is the technique of restriction fragment length polymorphism based PCR ("PCR-RFLP"), where nucleic acid sequences are amplified, treated with restriction enzymes, and separated by electrophoresis, allowing for the detection of nucleic acids containing small modifications, such as point mutations.

The terms "detect" and "analyze" in relation to a nucleic acid sequence, refer to the use of any method of observing, ascertaining or quantifying signals indicating the presence of the target nucleic acid sequence in a sample or the absolute or relative quantity of that target nucleic acid sequence in a sample. Methods can be combined with nucleic acid labeling methods to provide a signal by, for example: fluorescence, radioactivity, colorimetry, gravimetry, X-ray diffraction or adsorption, magnetism, enzymatic activity and the like. The signal can then be detected and/or quantified, by methods appropriate to the type of signal, to determine the presence or absence, of the specific DNA sequence of interest.

To "quantify" in relation to a nucleic acid sequence, refers to the use of any method to study the amount of a particular nucleic acid sequence, including, without limitation, methods to determine the number of copies of a nucleic acid sequence or to determine the change in quantity of copies of the nucleic acid sequence over time, or to determine the relative concentration of a sequence when compared to another sequence.

To assist in detection and analysis, specific DNA sequences can be "amplified" in a number of ways, including, but not limited to cycling probe reaction (Bekkaoui, F. et al, BioTechniques 20, 240-248 (1996), polymerase chain reaction (PCR), nested PCR, PCR-SSCP (single strand conformation polymorphism), ligase chain reaction (LCR) (F. Barany Proc. Natl. Acad. Sci USA 88:189-93 (1991)), cloning, strand displacement amplification (SDA) (G. K. Terrance Walker et al., Nucleic Acids Res. 22:2670-77 (1994), and variations such as allele-specific amplification (ASA).

An alternative to amplification of a specific DNA sequence that can be used to indicate the presence of that sequence in methods of the present invention is based on hybridization of a nucleic acid cleavage structure with the specific sequence, followed by cleavage of the cleavage structure in a site-specific manner. This method is herein referred to as "cleavage product detection." This method is described in detail in U.S. Pat. Nos. 5,541,331 and 5,614,402, and PCT publication Nos. WO 94/29482 and WO 97/27214. It allows for the detection of small amounts of specific nucleic acid sequences without amplifying the DNA sequence of interest.

The methods of the present invention provide a significant increase in sensitivity for analyzing cell-free, ultra short (20-50 base pairs), nucleic acids.

One method of detecting and analyzing specific ultra short DNA targets utilizes specific primers with internally labeled fluorophores. In one example, primer pairs were designed specifically for the ultra short DNA target of interest such that the primer binding sites lacking any intervening sequences in the double stranded PCR product. That is, the primer target sequences are immediately adjacent to each other or overlapping. The each of the primers in the primer pair are internally labeled with a fluorophore near 3'-end.

Appropriate fluorophores are selected from those known in the art. In some embodiments, the fluorophores are 6-carboxyfluorescein and carboxy-X-rhodamine. Preferably, the two bases closest to the 3' end are unlabeled to ensure unhindered initiation of the DNA polymerization reaction. The fluorophores are spaced such that 6-11 bases are between the fluorophores on the two primers. Preferably, the spacing between fluorophores is 6-10 bases. Following binding of the labeled primers, and inclusion of the appropriate materials required for PCR amplification, a PCR reaction amplifies the target sequence generating double-stranded oligonucleotide products, trans-labeled with the two fluorophores in close proximity. Amplified labeled product is then detected by Förster resonance energy transfer (FRET)-dependent fluorescence. In some embodiments, non-specific products are differentiated from specific products by measuring melting (dissociation) temperature. Example 1 and FIG. 2 describe these primers and the subsequent amplification reaction.

Another method of detecting and analyzing specific ultra short DNA targets utilizes specific primers comprising oligonucloetide tails at the 5' ends of their target-binding sequences. These oligonucleotide tails are labeled at their 5' ends with appropriate fluorophores. The oligonucleotide tails have no homology to any other sequences in the reaction, except short sequences adjacent to the fluorophores that are designed to be complementary to sequences on the opposite primer pair oligonucleotide tail, such that, if the two oligonucleotide tails are brought into close proximity, they will bind to each other. Each primer in the primer pair contains a replication blocking base to separate the target-binding region from the oligonucleotide tail comprising the fluorophore. This ensures that the tails are not replicated during PCR and remain single stranded. Any replication blocking base known in the art may be utilized, such as, iso-dC. Following binding of the labeled primers, and inclusion of the appropriate materials required for PCR amplification, and a PCR reaction amplifies the target sequence generating double-stranded oligonucleotide products. The complementary sequences of the oligonucleotide tails anneal, bringing the fluorophore pairs into close proximity. The amplified labeled product is then detected by FRET-dependent fluorescence. Fluorescence is measured at a temperature at which sticky ends are annealed only if they are part of the same double-stranded PCR product molecule. Example 2 and FIG. 7 describe these primers and the subsequent amplification reaction.

Another method of detecting and analyzing specific ultra short DNA targets utilizes three sequence-specific components, including a TaqMan probe. This method permits for very short amplicons by means of a partial target recognition sequence overlap of the TaqMan probe with the sense (same-strand) target-specific primer. This method utilizes a two stage, single tube, qPCR scheme. In stage 1, the target DNA is which is amplified using primers P1 and P2, which map in very close proximity to each other on the target sequence, thus allowing for very short templates. Primer P1 carries a target-unrelated 5'-end extension sequence, which is incorporated into the intermediate PCR products IP1/IP2 along with the template sequence. The resulting intermediate PCR product IP2 is sufficiently long to serve as template in stage 2, which involves primers P3 and P2 and a TaqMan probe Pr, which is labeled with fluorophore and quencher.

The mechanics of stage 2 are largely identical to those of a standard TaqMan qPCR assay. During this stage, as in a standard TaqMan qPCR assay, the amount of the final PCR product is monitored by measuring the increase in fluorescence of the PCR mixture. The three target-specific components in the assay are primers P3 and P2 and the TaqMan probe (Pr). Determination of the annealing temperatures ($T_a$) of the participant oligonucleotides, their concentrations, extension temperatures, and the number of cycles in each stage is an important part of assay development. The resulting assay proved to be exceptionally sensitive, highly sequence-specific, and suitable for the detection of target fragments as short as 20 to 50 bases ("ultra short" targets).

When choosing among potential targets, preference was given to those located in genomic sequence regions of relatively high $T_m$, which allow for the design of correspondingly short primers and probes. The $T_m$ of the probe Pr-PCR product complex was chosen to be 68° C. to 70° C. The $T_m$ of the target recognition sequences of primers P2 and P3 were chosen to be 8° C. to 10° C. below that of probe Pr, as they would normally be in a standard TaqMan assay. The $T_m$ of the target recognition sequence of primer P1 was chosen to be 8° C. to 10° C. below that of primers P2 and P3 to allow control of the length of each stage by altering the annealing/extension phase temperature. This low $T_m$ requirement also allows for very short target recognition sequence of in primer P1, thus reducing the minimum required overall length of the template. This method is shown schematically in FIG. 8 and described in Example 3.

In preferred example of the method described above, the P1 primer is further modified such that it is in a folded, stem-loop configuration and maintains that structure at the annealing/extension phase temperature of stage 2. This achieves better linearity of the assay, as it prevents primer P1 from competing for template with probe Pr in stage 2. Further, the stem loop region further comprises a replication blocking base known in the art. The inclusion of a replication blocking base prevents the stem loop region from being copied into the PCR product. In one example, the replication blocking base is iso-dC. This method is shown schematically in FIG. 10 and described in Example 4.

Without limiting the present invention to any specific methods of detection, analysis or quantification of methylated regions of DNA, the following techniques are useful for evaluating DNA methylation. Methods for the mapping and quantification of methylated regions of DNA, in general, and for analysis of transrenal DNA, in particular, may be grouped in two classes: methods allowing to assess overall methylation status of CpG islands and methods for analysis of sequence specific methylation.

Methods in the first group rely on Southern hybridization approach, based on utilization of properties of methylation sensitive restriction nucleases. Hatada et al., describes a genomic scanning method for higher organisms using restriction sites as landmarks (Proc Natl Acad Sci USA 88(21):9523-7, 1991). Issa et al., shows that methylation of the oestrogen receptor CpG island links ageing and neoplasia in human colon (Nat Genet (4):536-40, 1994). Pogribny and Yi, describe a sensitive new method for rapid detection of abnormal methylation patterns in global DNA with and within CpG islands (Biochem Biophys Res Commun 262 (3):624-8, 1999).

Recently designed DNA microarray based technology can also be included in this group. Huang et al., describes methylation profiling of CpG islands in human breast cancer cells (Genet (3):459-70, 1999).

The methods in the second group are based on registration of the sequence differences between methylated and unmethylated alleles resulting from bisulfite treatment of DNA.

Registration usually is carried out by PCR amplification using primers specific to methylated and unmethylated DNA. Herman et al., describes methylation-specific PCR: a novel PCR assay for methylation status of CpG islands (Proc Natl Acad Sci USA 93(18):9821-6, 1996). Depending on the experimental setting several approaches based on this strategy have been developed.

There are also several options for the quantification of methylated CpG islands in small amount of DNA (Xiong and Laird, Nucleic Acids Res 25(12):2532-4, 1997, describing COBRA: a sensitive and quantitative DNA methylation assay, and Olek et al., Nucleic Acids Res 24(24):5064-6, 1996, describing a modified and improved method for bisulphite based cytosine methylation analysis) and partially degraded DNA received from micro-dissected pathology sections (Gonzalgo and Jones, Nucleic Acids Res 25(12): 2529-31, 1997, describing rapid quantitation of methylation differences at specific sites using methylation-sensitive single nucleotide primer extension (Ms-SNuPE)). Additionally, there is a methylation sensitive SSCP that was developed for the analysis multiple methylation sites in CpG islands (Kinoshita et al., Anal Biochem 278(2):165-9, 2000, describing methods for screening hypermethylated regions by methylation-sensitive single-strand conformational polymorphism) and an extremely sensitive methylation specific Real Time PCR (Eads et al., Nucleic Acids Res 28(8): E32, 2000, describing MethyLight: a high-throughput assay to measure DNA methylation).

Ligation-mediated polymerase chain reaction (LMPCR) has been used for the detection of DNA adducts at individual nucleotide positions in mammalian genes. Adduct-specific enzymes, such as T4 endonuclease V, base excision repair enzymes, like UVTABC nuclease, and chemical cleavage can be used to convert the adducts into DNA strand breaks. The positions of these breaks are then detected by LMPCR. Yoon and Lee, Mol Cells 10(1):71-5, 2000, describes the mapping of altromycin B-DNA adduct at nucleotide resolution in the human genomic DNA by ligation-mediated PCR. Pfeifer, et al., Proc Natl Acad Sci USA 88(4):1374-8, 1991, describes the in vivo mapping of a DNA adduct at nucleotide resolution: detection of pyrimidine (6-4) pyrimidone photoproducts by ligation-mediated polymerase chain reaction. Pfeifer and Tang, Toxicol Left 102-130:447-51, 1998, describes PCR-based approaches to adduct analysis.

Using this approach the distribution of benzo[a]pyrene diol epoxide adducts (formed by cigarette smoke major carcinogen benzo[a]pyrene) in the P53 gene was mapped at nucleotide resolution. Adduct formation was observed at the nucleotide positions that appeared to be mutational hotspots in human lung cancers. Denissenko et al., Science 274 (5286):430-2, 1996, describes preferential formation of benzo[a]pyrene adducts at lung cancer mutational hotspots in P53. A similar trend was observed in the case of skin cancer. Tommasi et al., Cancer Res 57(21):4727-30, 1997, shows that sunlight induces pyrimidine dimers occur preferentially at 5-methylcytosine bases. Thus, the distribution of DNA adducts in the p53 gene caused by environmental carcinogens corresponds to the mutational hotspots of certain cancers.

These data indicate that both quantitation of DNA adducts and their gene specific nucleotide mapping in transrenal DNA can be used for the evaluation of genotoxic effects of environmental factors, dietary and other carcinogens as well as for prediction of resulting predisposition to a specific type of cancer.

To facilitate understanding of the invention, a number of terms are defined below.

The term "gene" refers to a DNA sequence that comprises control and coding sequences necessary for the transcription of an RNA sequence. The term "genome" refers to the complete gene complement of an organism, contained in a set of chromosomes in eukaryotes.

The term "ultra short" refers to a DNA or RNA sequence of less than 50 nucleotides. Preferably, less than 45 nucleotides, less than 40 nucleotides, less than 35 nucleotides, less than 30 nucleotides, less than 25 nucleotides, less than 20 nucleotides, less than 15 nucleotides, less, than 10 nucleotides, less than 5 nucleotides. More preferably, the DNA or RNA sequence is between 20 and 50 nucleotides.

A "wild-type" gene or gene sequence is that which is most frequently observed in a population and is thus arbitrarily designed the "normal" or "wild-type" form of the gene. In contrast, the term "modified", "mutant", "anomaly" or "altered" refers to a gene, sequence or gene product which displays modifications in sequence and or functional properties (i.e., altered characteristics) when compared to the wild-type gene, sequence or gene product. For example, an altered sequence detected in the urine of a patient can display a modification that occurs in DNA sequences from tumor cells and that does not occur in the patient's normal (i.e. non cancerous) cells. It is noted that naturally-occurring mutants can be isolated; these are identified by the fact that they have altered characteristics when compared to the wild-type gene or gene product. Without limiting the invention to the detection of any specific type of anomaly, mutations can take many forms, including addition, addition-deletion, deletion, frame-shift, missense, point, reading frame shift, reverse, transition and transversion mutations as well as microsatellite alterations.

A "disease associated genetic anomaly" refers to a gene, sequence or gene product that displays modifications in sequence when compared to the wild-type gene and that is indicative of the propensity to develop or the existence of a disease in the carrier of that anomaly. A disease associated genetic anomaly encompasses, without limitation, inherited anomalies as well as new mutations.

The term "unique fetal DNA sequence" is defined as a sequence of nucleic acids that is present in the genome of the fetus, but not in the maternal genome.

The terms "oligonucleotide" and "polynucleotide" and "polymeric" nucleic acid are interchangeable and are defined as a molecule comprised of two or more deoxyribonucleotides or ribonucleotides, preferably more than three, and usually more than ten. The exact size will depend on many factors, which in turn depends on the ultimate function or use of the oligonucleotide. The oligonucleotide can be generated in any manner, including chemical synthesis, DNA replication, reverse transcription, or a combination thereof.

Because mononucleotides are reacted to make oligonucleotides in a manner such that the 5' phosphate of one mononucleotide pentose ring is attached to the 3' oxygen of its neighbor in one direction via a phosphodiester linkage, an end of an oligonucleotide is referred to as the "5' end" if its 5' phosphate is not linked to the 3' oxygen of a mononucleotide pentose ring and as the "3' end" if its 3' oxygen is not linked to a 5' phosphate of a subsequent mononucleotide pentose ring. As used herein, a nucleic acid sequence, even if internal to a larger oligonucleotide, also can be said to have 5' and 3' ends.

When two different, non-overlapping oligonucleotides anneal to different regions of the same linear complementary nucleic acid sequence, and the 3' end of one oligonucleotide points towards the 5' end of the other, the former can be called the "upstream" oligonucleotide and the latter the "downstream" oligonucleotide.

The term "primer" refers to an oligonucleotide which is capable of acting as a point of initiation of synthesis when placed under conditions in which primer extension is initiated. An oligonucleotide "primer" can occur naturally, as in a purified restriction digest or be produced synthetically.

A primer is selected to be "substantially" complementary to a strand of specific sequence of the template. A primer must be sufficiently complementary to hybridize with a template strand for primer elongation to occur. A primer sequence need not reflect the exact sequence of the template. For example, a non-complementary nucleotide fragment can be attached to the 5' end of the primer, with the remainder of the primer sequence being substantially complementary to the strand. Non-complementary bases or longer sequences can be interspersed into the primer, provided that the primer sequence has sufficient complementarity with the sequence of the template to hybridize and thereby form a template primer complex for synthesis of the extension product of the primer.

A "target" nucleic acid is a nucleic acid sequence to be evaluated by hybridization, amplification or any other means of analyzing a nucleic acid sequence, including a combination of analysis methods.

"Hybridization" methods involve the annealing of a complementary sequence to the target nucleic acid (the sequence to be analyzed). The ability of two polymers of nucleic acid containing complementary sequences to find each other and anneal through base pairing interaction is a well-recognized phenomenon. The initial observations of the "hybridization" process by Marmur and Lane, Proc. Natl. Acad. Sci. USA 46:453 (1960) and Doty et al., Proc. Natl. Acad. Sci. USA 46:461 (1960) have been followed by the refinement of this process into an essential tool of modern biology. Hybridization encompasses, but is not limited to, slot, dot and blot hybridization techniques.

It is important for some diagnostic applications to determine whether the hybridization represents complete or partial complementarity. For example, where it is desired to detect simply the presence or absence of pathogen DNA (such as from a virus, bacterium, fungi, mycoplasma, protozoan) it is only important that the hybridization method ensures hybridization when the relevant sequence is present; conditions can be selected where both partially complementary probes and completely complementary probes will hybridize. Other diagnostic applications, however, could require that the hybridization method distinguish between partial and complete complementarity. It may be of interest to detect genetic polymorphisms.

Methods that allow for the same level of hybridization in the case of both partial as well as complete complementarity are typically unsuited for such applications; the probe will hybridize to both the normal and variant target sequence. The present invention contemplates that for some diagnostic purposes, hybridization be combined with other techniques (such as restriction enzyme analysis). Hybridization, regardless of the method used, requires some degree of complementarity between the sequence being analyzed (the target sequence) and the fragment of DNA used to perform the test (the probe). (Of course, one can obtain binding without any complementarity but this binding is nonspecific and to be avoided.)

The complement of a nucleic acid sequence as used herein refers to an oligonucleotide which, when aligned with the nucleic acid sequence such that the 5' end of one sequence is paired with the 3' end of the other, is in "antiparallel association." Specific bases not commonly found in natural nucleic acids can be included in the nucleic acids of the present invention and include, for example, inosine and 7-deazaguanine. Complementarity need not be perfect; stable duplexes can contain mismatched base pairs or unmatched bases. Those skilled in the art of nucleic acid technology can determine duplex stability empirically considering a number of variables including, for example, the length of the oligonucleotide, base composition and sequence of the oligonucleotide, ionic strength and incidence of mismatched base pairs.

As used herein, the term "Tm" is used in reference to the "melting temperature." The melting temperature is the temperature at which a population of double-stranded nucleic acid molecules becomes half dissociated into single strands. The equation for calculating the Tm of nucleic acids is well known in the art. As indicated by standard references, a simple estimate of the Tm value can be calculated by the equation: $Tm=81.5+0.41(\% G+C)$, when a nucleic acid is in aqueous solution at 1 M NaCl (see e.g., Anderson and Young, Quantitative Filter Hybridisation, in Nucleic Acid Hybridisation (1985). Other references include more sophisticated computations which take structural as well as sequence characteristics into account for the calculation of Tm.

The term "probe" as used herein refers to an oligonucleotide (i.e., a sequence of nucleotides), whether occurring naturally as in a purified restriction digest or produced synthetically, which forms a duplex structure or other complex with a sequence in another nucleic acid, due to complementarity or other means of reproducible attractive interaction, of at least one sequence in the probe with a sequence in the other nucleic acid. Probes are useful in the detection, identification and isolation of particular gene sequences. It is contemplated that any probe used in the present invention will be labeled with any "reporter molecule," so that it is detectable in any detection system, including, but not limited to, enzyme (e.g., ELISA, as well as enzyme-based histochemical assays), fluorescent, radioactive, and luminescent systems. It is further contemplated that the oligonucleotide of interest (i.e., to be detected) will be labeled with a reporter molecule. It is also contemplated that both the probe and oligonucleotide of interest will be labeled. It is not intended that the present invention be limited to any particular detection system or label.

The term "label" as used herein refers to any atom or molecule which can be used to provide a detectable (preferably quantifiable) signal, and which can be attached to a nucleic acid or protein. Labels provide signals detectable by any number of methods, including, but not limited to, fluorescence, radioactivity, colorimetry, gravimetry, X-ray diffraction or absorption, magnetism, and enzymatic activity.

The term "substantially single-stranded" when used in reference to a nucleic acid target means that the target molecule exists primarily as a single strand of nucleic acid in contrast to a double-stranded target which exists as two strands of nucleic acid which are held together by interstrand base pairing interactions.

The term "sequence variation" as used herein refers to differences in nucleic acid sequence between two nucleic acid templates. For example, a wild-type structural gene and a mutant form of this wild-type structural gene can vary in sequence by the presence of single base substitutions and/or deletions or insertions of one or more nucleotides. These two forms of the structural gene are said to vary in sequence from one another. A second mutant form of the structural gene can exit. This second mutant form is said to vary in sequence from both the wild-type gene and the first mutant form of the gene.

The terms "structure probing signature," "hybridization signature" and "hybridization profile" are used interchangeably herein to indicate the measured level of complex formation between a target nucleic acid and a probe or set of probes, such measured levels being characteristic of the target nucleic acid when compared to levels of complex formation involving reference targets or probes.

"Oligonucleotide primers matching or complementary to a gene sequence" refers to oligonucleotide primers capable of facilitating the template-dependent synthesis of single or double-stranded nucleic acids. Oligonucleotide primers matching or complementary to a gene sequence can be used in PCRs, RT-PCRs and the like.

"Nucleic acid sequence" as used herein refers to an oligonucleotide, nucleotide or polynucleotide, and fragments or portions thereof, and to DNA or RNA of genomic or synthetic origin which can be single- or double-stranded, and represent the sense or antisense strand.

A "deletion" is defined as a change in either nucleotide or amino acid sequence in which one or more nucleotides or amino acid residues, respectively, are absent.

An "insertion" or "addition" is that change in a nucleotide or amino acid sequence which has resulted in the addition of one or more nucleotides or amino acid residues, respectively, as compared to, naturally occurring sequences.

A "substitution" results from the replacement of one or more nucleotides or amino acids by different nucleotides or amino acids, respectively.

A "modification" in a nucleic acid sequence refers to any change to a nucleic acid sequence, including, but not limited to a deletion, an addition, an addition-deletion, a substitution, an insertion, a reversion, a transversion, a point mutation, a microsatellite alteration, methylation or nucleotide adduct formation.

As used herein, the terms "purified", "decontaminated" and "sterilized" refer to the removal of contaminant(s) from a sample.

As used herein, the terms "substantially purified" and "substantially isolated" refer to nucleic acid sequences that are removed from their natural environment, isolated or separated, and are preferably 60% free, more preferably 75% free, and most preferably 90% free from other components with which they are naturally associated. An "isolated polynucleotide" is therefore a substantially purified polynucleotide. It is contemplated that to practice the methods of the present invention polynucleotides can be, but need not be substantially purified. A variety of methods for the detection of nucleic acid sequences in unpurified form are known in the art.

"Amplification" is defined as the production of additional copies of a nucleic acid sequence and is generally carried out using polymerase chain reaction or other technologies well known in the art (e.g., Dieffenbach and Dveksler, PCR Primer, a Laboratory Manual, Cold Spring Harbor Press, Plainview, N.Y. [1995]). As used herein, the term "polymerase chain reaction" ("PCR") refers to the method of K. B. Mullis (U.S. Pat. Nos. 4,683,195 and 4,683,202, hereby incorporated by reference), which describe a method for increasing the concentration of a segment of a target sequence in a mixture of genomic DNA without cloning or purification. This process for amplifying the target sequence consists of introducing a large excess of two oligonucleotide primers to the DNA mixture containing the desired target sequence, followed by a precise sequence of thermal cycling in the presence of a DNA polymerase. The two primers are complementary to their respective strands of the double stranded target sequence. To effect amplification, the mixture is denatured and the primers then annealed to their complementary sequences within the target molecule. Following annealing, the primers are extended with a polymerase so as to form a new pair of complementary strands. The steps of denaturation, primer annealing and polymerase extension can be repeated many times (i.e., denaturation, annealing and extension constitute one "cycle"; there can be numerous "cycles") to obtain a high concentration of an amplified segment of the desired target sequence. The length of the amplified segment of the desired target sequence is determined by the relative positions of the primers with respect to each other, and therefore, this length is a controllable parameter. By virtue of the repeating aspect of the process, the method is referred to as the "polymerase chain reaction" (hereinafter "PCR"). Because the desired amplified segments of the target sequence become the predominant sequences (in terms of concentration) in the mixture, they are said to be "PCR amplified".

As used herein, the term "polymerase" refers to any enzyme suitable for use in the amplification of nucleic acids of interest. It is intended that the term encompass such DNA polymerases as Taq DNA polymerase obtained from Thermus aquaticus, although other polymerases, both thermostable and thermolabile are also encompassed by this definition.

With PCR, it is possible to amplify a single copy of a specific target sequence in genomic DNA to a level that can be detected by several different methodologies (e.g., staining, hybridization with a labeled probe; incorporation of biotinylated primers followed by avidin-enzyme conjugate detection; incorporation of 32P-labeled deoxynucleotide triphosphates, such as dCTP or dATP, into the amplified segment). In addition to genomic DNA, any oligonucleotide sequence can be amplified with the appropriate set of primer molecules. In particular, the amplified segments created by the PCR process itself are, themselves, efficient templates for subsequent PCR amplifications. Amplified target sequences can be used to obtain segments of DNA (e.g., genes) for insertion into recombinant vectors.

As used herein, the terms "PCR product" and "amplification product" refer to the resultant mixture of compounds after two or more cycles of the PCR steps of denaturation, annealing and extension are complete. These terms encompass the case where there has been amplification of one or more segments of one or more target sequences.

As used herein, the terms "restriction endonucleases" and "restriction enzymes" refer to bacterial enzymes, each of which cut double-stranded DNA at or near a specific nucleotide sequence.

As used herein, the terms "complementary" or "complementarity" are used in reference to polynucleotides (i.e., a sequence of nucleotides) related by the base-pairing rules. For example, for the sequence "A-G-T," is complementary to the sequence "T-C-A." Complementarity can be "partial," in which only some of the nucleic acids' bases are matched according to the base pairing rules. Or, there can be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods that depend upon binding between nucleic acids.

The term "homology" refers to a degree of complementarity. There can be partial homology or complete homology (i.e., identity). A partially complementary sequence is one that at least partially inhibits a completely complementary sequence from hybridizing to a target nucleic acid is referred to using the functional term "substantially homologous." The inhibition of hybridization of the completely complementary sequence to the target sequence can be examined using a hybridization assay (Southern or Northern blot, solution hybridization and the like) under conditions of low stringency. A substantially homologous sequence or probe will compete for and inhibit the binding (i.e., the hybridization) of a completely homologous to a target under conditions of low stringency. This is not to say that conditions of low stringency are such that are non-specific binding is permitted; low stringency conditions require that the binding of two sequences to one another be a specific (i.e., selective) interaction. The absence of non-specific binding can be tested by the use of a second target which lacks even a partial degree of complementarity (e.g., less than about 30% identity); in the absence of non-specific binding the probe will not hybridize to the second non-complementary target.

Numerous equivalent conditions can be employed to comprise either low or high stringency conditions; factors such as the length and nature (DNA, RNA, base composition) of the probe and nature of the target (DNA, RNA, base composition, present in solution or immobilized, etc.) and the concentration of the salts and other components (e.g., the presence or absence of formamide, dextran sulfate, polyethylene glycol) are considered and the hybridization solution can be varied to generate conditions of either low or high stringency hybridization different from, but equivalent to, the above listed conditions. The term "hybridization" as used herein includes "any process by which a strand of nucleic acid joins with a complementary strand through base pairing" (Coombs, Dictionary of Biotechnology, Stockton Press, New York N.Y. [1994].

"Stringency" typically occurs in a range from about Tm-5° C. (5° C. below the Tm of the probe) to about 20° C. to 25° C. below Tm. As will be understood by those of skill in the art, a stringent hybridization can be used to identify or detect identical polynucleotide sequences or to identify or detect similar or related polynucleotide sequences.

As used herein the term "hybridization complex" refers to a complex formed between two nucleic acid sequences by virtue of the formation of hydrogen bonds between complementary G and C bases and between complementary A and T bases; these hydrogen bonds can be further stabilized by base stacking interactions. The two complementary nucleic acid sequences hydrogen bond in an antiparallel configuration. A hybridization complex can be formed in solution (e.g., C0t or R0t analysis) or between one nucleic acid sequence present in solution and another nucleic acid sequence immobilized to a solid support (e.g., a nylon membrane or a nitrocellulose filter as employed in Southern and Northern blotting, dot blotting or a glass slide as employed in situ hybridization, including FISH [fluorescent in situ hybridization]).

As used herein, the term "antisense" is used in reference to RNA sequences which are complementary to a specific RNA (e.g., mRNA) or DNA sequence. Antisense RNA can be produced by any method, including synthesis by splicing the gene(s) of interest in a reverse orientation to a viral promoter which permits the synthesis of a coding strand. Once introduced into a cell, this transcribed strand combines with natural mRNA produced by the cell to form duplexes. These duplexes then block either further transcription of the mRNA or its translation. In this manner, mutant phenotypes can be generated. The term "antisense strand" is used in reference to a nucleic acid strand that is complementary to the "sense" strand. The designation (−) (i.e., "negative") is sometimes used in reference to the antisense strand, with the designation (+) sometimes used in reference to the sense (i.e., "positive") strand.

The term "sample" as used herein is used in its broadest sense. A biological sample suspected of containing nucleic acid can comprise, but is not limited to, genomic DNA (in solution or bound to a solid support such as for Southern blot analysis), cDNA (in solution or bound to a solid support), and the like.

The term "urinary tract" as used herein refers to the organs and ducts which participate in the secretion and elimination of urine from the body.

The terms "transrenal DNA" and "transrenal nucleic acid" as used herein refer to nucleic acids that have crossed the kidney barrier. Transrenal DNA as used herein differs from miRNA. Specifically, transrenal DNA comprises randomness in the 3' and 5' ends, which is not present in miRNA.

The present invention encompasses a platform for the detection and gene specific analysis of "ultra short" transrenal DNA fragments carrying different nucleotide lesions and adducts caused by various external and internal DNA modifying factors. Without limiting the scope of the invention, but in the interest of clarity, some factors that generate DNA modifications might be grouped in three classes: (i) physical, including but not limited to gamma and UV irradiation, temperature fluctuations; (ii) chemical, including but not limited to environmental pollutants, naturally occurring genotoxins, carcinogens, anticancer drugs and (iii) reactive metabolites such as active forms of oxygen, lipid peroxidation products and hydrolytic agents.

The invention is further described below, by way of the following examples. The examples also illustrate useful methodology for practicing the invention. These examples do not limit the claimed invention.

EXAMPLES

Example 1

Example 1 shows the design of primers with internally located fluorophores for detection of ultra short DNA targets by PCR using fret-dependent fluorescence.

The specificity of a typical labeled-primer qPCR assay is determined solely by the specificity of the two primers, and therefore such an assay is not capable of distinguishing between templates having identical primer binding sites but different intervening sequences. To detect very short target fragments and overcome this limitation, novel labeled-primer assays were developed specific for targets in which the primer binding sites are either immediately adjacent to each other or even slightly overlapping, thus lacking any intervening sequences. Such amplicons are characterized by the pair of primer-derived sequences positioned in close proximity to each other in the double-stranded PCR product. In the assay, the mutual proximity of fluorescently labeled oligonucleotides was detected by Förster resonance energy transfer (FRET) between them. To test the effectiveness of a FRET assay, a model system was designed consisting of two primers internally labeled with a widely used FRET fluorophore pair, 6-carboxyfluorescein (FAM) and carboxy-X-rhodamine (ROX).

| Direction | ID | Template | SEQ ID NO: |
|---|---|---|---|
| Forward primer: | ES0343-FL | 5'-CGTCCGTGCTGTCGACG-[FL-dT]-AG-3' | 1 |
| Reverse primer: | ES0344-RX | 5'-CATACCACGCCATCAGAG-[ROX-dT]-GC-3' | 2 |

Figure 2:
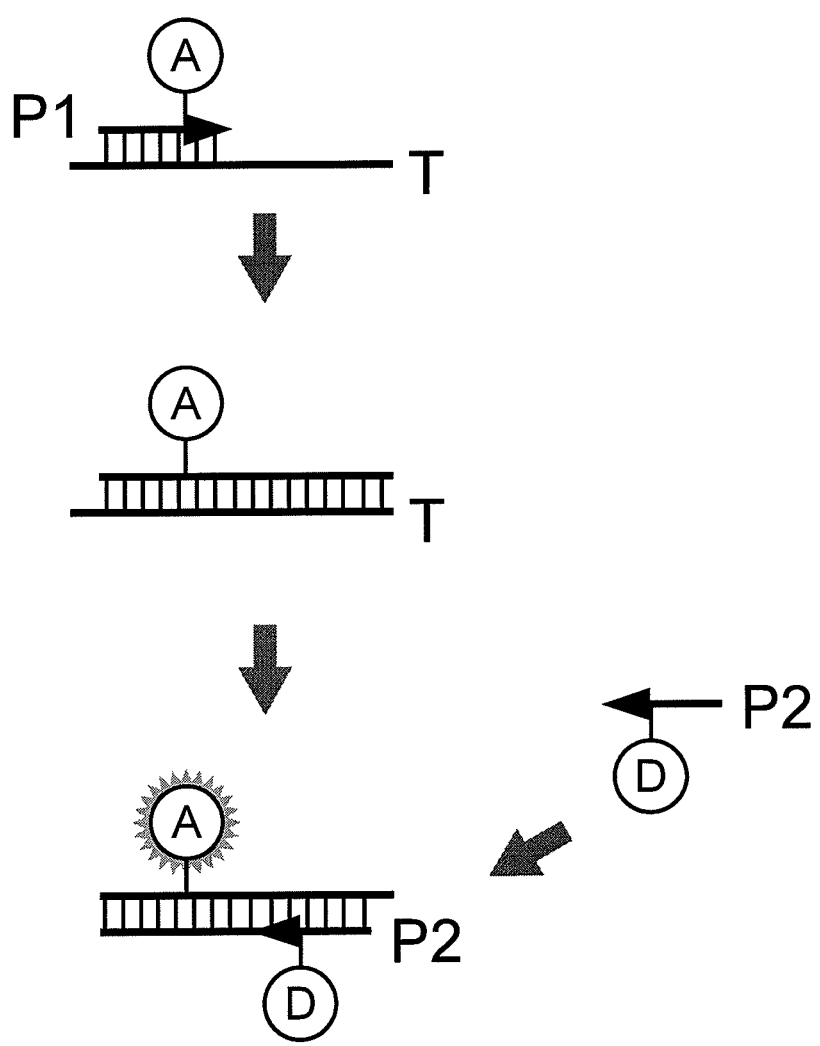
FIG. 2 is a schematic showing FRET-based PCR with primers labeled with fluorophores near the 3'-end.

As shown in FIG. 2, each fluorophore was conjugated to a thymine base at position 3 from the 3' end of each primer. In FIG. 2, T designates a template; P1 and P2 designate primers; D and A designate donor and acceptor fluorophores, respectively. Labeling the primers at internal bases and leaving at least the 2 bases closest to the 3' end unlabeled is necessary to ensure unhindered initiation of DNA polymerization reaction (Ahmad and Ghasemi, Anal Bioanal Chem. 387:2737-43, 2007). This model system was utilized to determine the spacing between the fluorophores that yields the highest FRET efficiency by testing it on a number of oligonucleotide templates with a range of spacing between the 2 primer binding sites.

| TEMPLATE | FLUORO-PHORE SPACING | SEQ ID NO: |
|---|---|---|
| 5'-CAGCACGTCCGTGCTGTCGACGTAGACATCA GCACTCTGATGGCGTGGTATGACGAC-3' | 11 | 3<br>4 |
| 5'-CAGCACGTCCGTGCTGTCGACGTAGCATCAG CACTCTGATGGCGTGGTATGACGAC-3' | 10 | 5<br>6 |
| 5'-CAGCACGTCCGTGCTGTCGACGTAGATCAGC ACTCTGATGGCGTGGTATGACGAC-3' | 9 | 7<br>8 |
| 5'-CAGCACGTCCGTGCTGTCGACGTAGATGC ACTCTGATGGCGTGGTATGACGAC-3' | 7 | 9<br>10 |
| 5'-CAGCACGTCCGTGCTGTCGACGTAGAGC ACTCTGATGGCGTGGTATGACGAC-3' | 6 | 11<br>12 |
| 5'-CAGCACGTCCGTGCTGTCGACGTAGGC ACTCTGATGGCGTGGTATGACGAC-3' | 5 | 13<br>14 |
| 5'-CAGCACGTCCGTGCTGTCGACGTAC ACTCTGATGGCGTGGTATGACGAC-3' | 4 | 15<br>16 |

Figure 3:
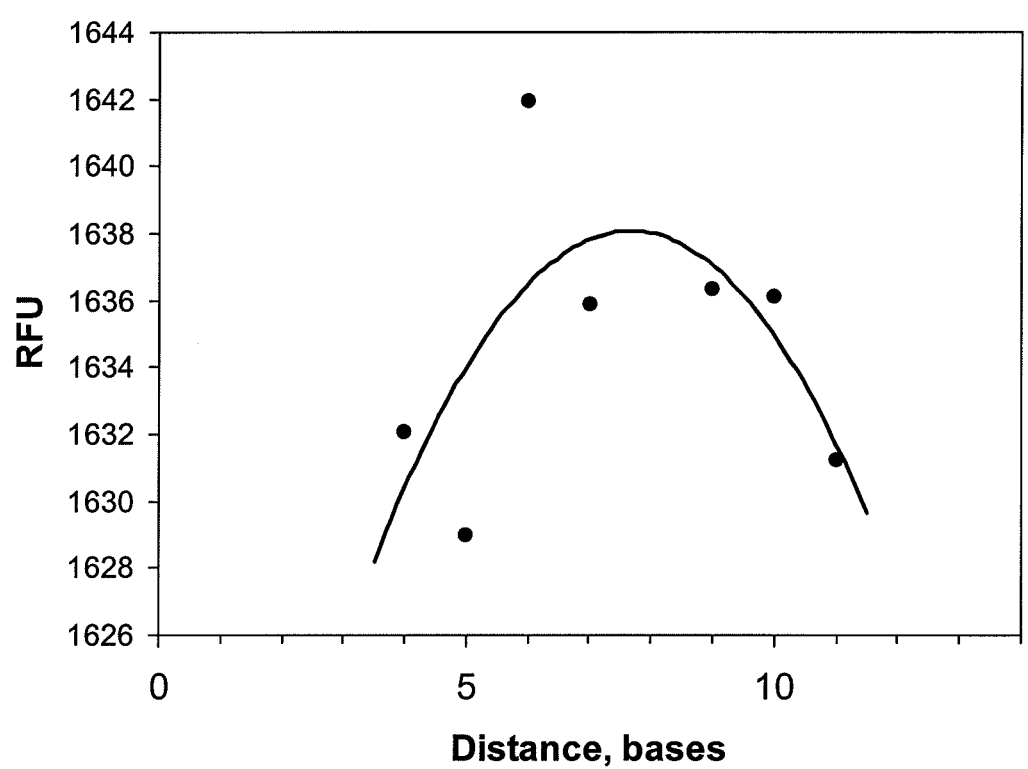
FIG. 3 is a graph showing dependence of fluorescence signal on the distance between the donor and acceptor fluorophores.

PCR generates a double-stranded oligonucleotide product trans-labeled with the 2 fluorophores, the spatial distance between which is assumed to directly correlate with the spacing between the primer binding sites on the supplied template. Although the signal variation for different templates was not very significant, FIG. 3 shows that a peak in FRET efficiency at fluorophore spacing of 6 to 10 bases in the PCR product. Based on the results in FIG. 3, the assay is capable of detecting very short target fragments, those containing both of the primer binding sites in immediate proximity to each other. The minimum length of target fragments detectable with this system is approximated by the combined length of the 2 primer binding sites, totaling about 20 to 50 bases.

This method was then tested for its ability to detect Epstein-Barr virus (EBV) BamHI-W region sequence. A pair of primers were designed and internally labeled with FAM and ROX, and PCR amplification of the target in real-time was monitored by measuring 610 nm fluorescence emission signal with excitation at 492 nm.

| Direction | ID | Template | SEQ ID NO |
|---|---|---|---|
| Forward primer: | ES0430-FL | 5'-ATCGCAGAGCCCAGGATG-[FL-dT]-CC-3' | 17 |
| Reverse primer: | ES0431-RX | 5'-ACGAGCTCTAGGGTCCCTTC-[ROX-dT]-GG-3' | 18 |
| 39-bp target | | 5'-CAGAGCCCAGGATGTCCCCCA GAAGGGACCCTAG-3' | 19 |

Figure 4:
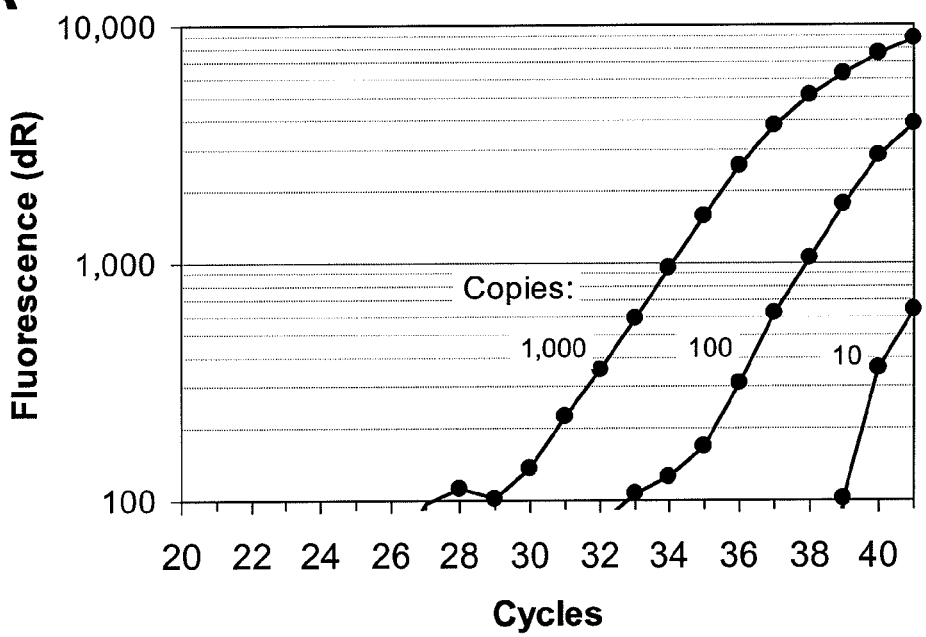
FIG. 4, Panel A, is a graph showing detection of EBV-specific sequences by FRET-based real-time PCR. Panel B shows a calibration curve.
Figure 4:
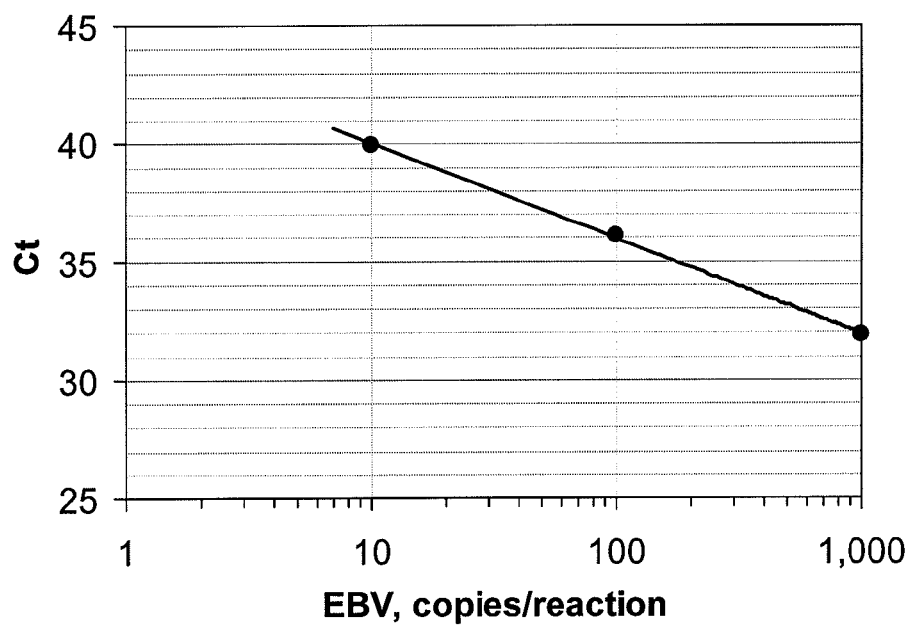

To monitor the level of fluorescence of individual fluorophores, fluorescence emission was also measured at 516 nm with 492 nm excitation (FAM), and emission at 610 nm with 585 nm excitation (ROX). No concurrent increase in the level of fluorescence of the individual fluorophores was observed in the reaction, indicating that all of the fluorescence increase (492 nm ex/610 nm em) was attributable to FRET between the fluorophores. FIG. 4 shows that this method permits the detection of as few as 10 copies of the target EBV sequence in a 25 µl reaction. Specifically, FIG. 4, Panel A shows amplification of EBV standards in labeled-primer FRET real-time PCR assay and FIG. 4, Panel B shows the calibration curve.

In another example of the application of labeled-primer FRET Real-Time PCR, a pair of fluorophore-labeled primers were designed for the detection of a chromosome Y-specific sequence. PCR with these 2 primers amplifies a 36-bp region of the SRY gene, yielding a product with the donor and acceptor fluorophores spaced 6 bases apart.

| Direction | ID | Template | SEQ ID |
|---|---|---|---|
| Forward primer: | ES0619-FL | 5'-CCGCAGATCCCGC-[FL-dT]-TCG-3' | 20 |
| Reverse primer: | ES0620-RX | 5'-GCACTTCGCTGCAGAG-[ROX-dT]-ACC-3' | 21 |
| 39-bp target | | 5'CCGCAGATCCCGCTTCGGTACT CTGCAGCGAAGTGC-3' | 22 |

Figure 5:
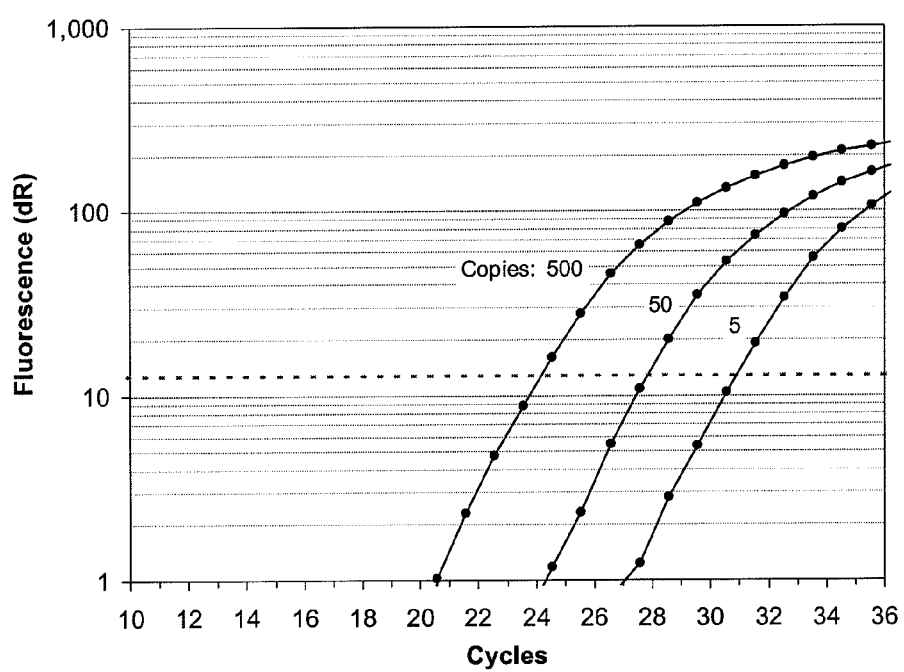
FIG. 5 is a graph showing amplification of a 36-bp SRY target in labeled-primer FRET real-time PCR assay.

FIG. 5 shows the amplification of the 36-bp SRY region as described above.

Figure 6:
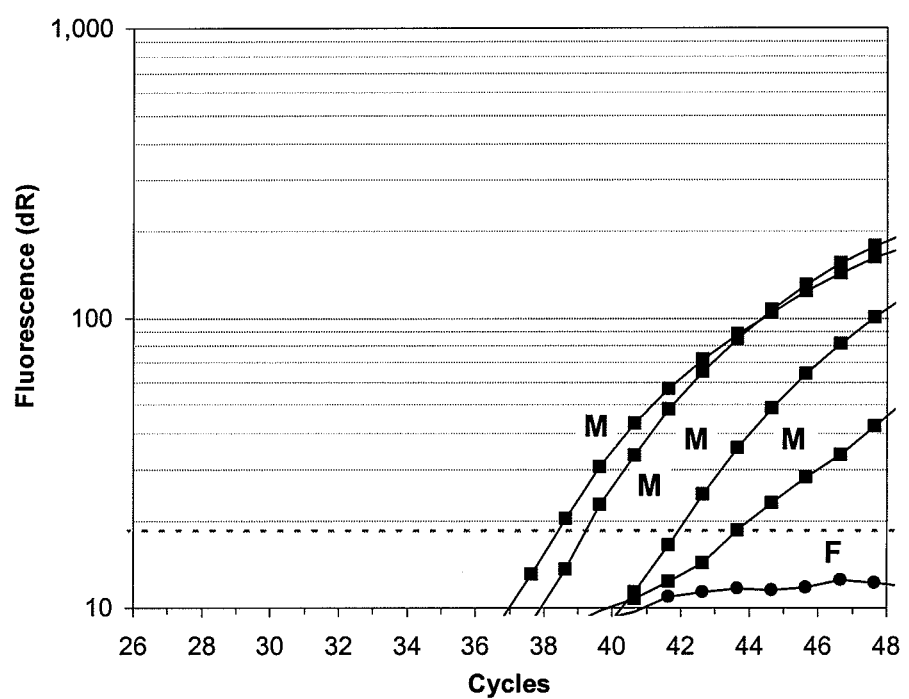
FIG. 6 is a graph showing fetal gender detection by labeled-primer FRET real-time PCR assay of DNA extracted from urine of pregnant women.

The FRET SRY assay was applied to DNA samples purified from the urine of pregnant women. The results in FIG. 6 show the detection of SRY sequences in samples from women pregnant with male fetuses, but not in a sample from a woman pregnant with a female fetus. In FIG. 6, M designates samples from women pregnant with male fetuses and F designates a sample from a woman pregnant with a female fetus.

The fluorescence signal detected by the labeled-primer FRET method indicated the presence of double-stranded products of amplification in which (i) both labeled primers are incorporated, and (ii) the primers are incorporated in such a manner that the fluorophores are positioned in close proximity to each other. In most cases, these two requirements are sufficient to ensure that only the specific PCR products generate detectable fluorescence signal. However, the downside of using a highly sensitive PCR method is the occasional, uncontrolled generation of nonspecific products, which may also give FRET-dependent fluorescence signal.

In conventional PCR, nonspecific products are typically differentiated by size using gel electrophoresis. The labeled-primer FRET method allows these nonspecific products to be differentiated by measuring their melting (dissociation) temperature. For example, a larger nonspecific product is likely to exhibit a higher melting temperature than that of the specific one. Since FRET takes place only when these products are in their double-stranded state, their transition to a single-stranded state is accompanied by a decrease in FRET fluorescence. Therefore, the temperature of this transition can be measured immediately after the amplification phase, with no need for any additional dye. The amplification phase and the melting phase fluorescence signals are based on the same FRET effect, thus ensuring that in both cases the same product is analyzed.

Example 2

Figure 7:
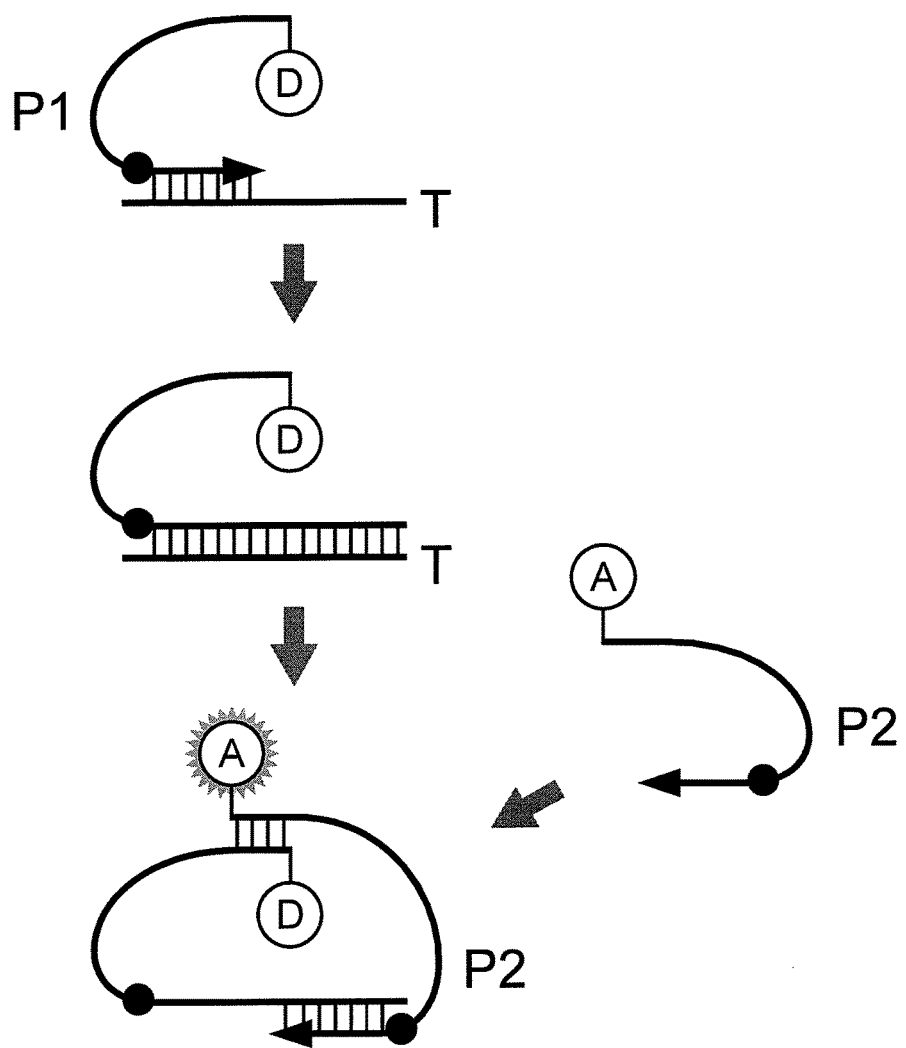
FIG. 7 is a schematic showing FRET-based PCR with primers having tails and labeled with fluorophores near the 5'-end.

Example 2 shows the design of primers with fluorophores located on 5'-end for detection of ultra short DNA targets by PCR using fret-dependent fluorescence Compared to unlabeled primers, the use of primers labeled with fluorophores near their 3' ends may lower the efficiency of the PCR, most likely due to reduction in polymerase processivity as it reads fluorophore-labeled bases of the primers incorporated into templates. To overcome this problem, another variant of the labeled-primer FRET qPCR scheme was developed. In this example, as shown in FIG. 7, the primers contain oligonucleotide tails at the 5' ends of their target-binding sequences. In FIG. 7, T designates a template; P1 and P2 designate primers; D and A designate donor and acceptor fluorophores, respectively; black circles denote the positions of replication-blocking modifications. The tails are labeled at their 5' ends with appropriate fluorophores, so that each double-stranded PCR product molecule carries a FRET fluorophore pair. On each primer, the tail is separated from target-binding region by a replication-blocking base, such as iso-dC, to ensure that the tails are not replicated during the PCR, and thus remain single-stranded. The tails are chosen to have no homology to any other sequence in the system, except that short sequence stretches immediately adjacent to the fluorophores are designed to be complementary to each other (sticky ends). Annealing of the sticky ends brings the fluorophores of the FRET pair into close proximity to each other. Due to their increased local concentration, these sticky ends are expected to anneal more readily when both are part of the same double-stranded PCR product. Fluorescence is measured at a temperature at which sticky ends are annealed only if they are part of the same double-stranded PCR product molecule. The intensity of FRET fluorescence measured at this temperature directly correlates to the yield of PCR product. Nonspecific PCR products of significantly greater length should not contribute to the FRET fluorescence signal because their sticky ends are too far apart to anneal to each other.

A model system was designed to test this version of labeled-primer assay. Two "primer" oligonucleotides labeled on their 5' ends with FAM and ROX dyes, respectively, were mixed together and added to a range of "template" oligonucleotides, and the dissociation curves of the mixtures were measured. The templates contained sequences complementary to each of the two primers, and differed in the distance between those sequences. The dissociation curves were generated for each mixture. An increased FRET signal from the labeled oligonucleotides in the presence of the "templates" was observed, showing that it is possible to detect incorporation of the labeled primers into PCR products.

Example 3

Example 3 shows the design of single-tube PCR scheme for detection of ultra short DNA targets.

Figure 8:
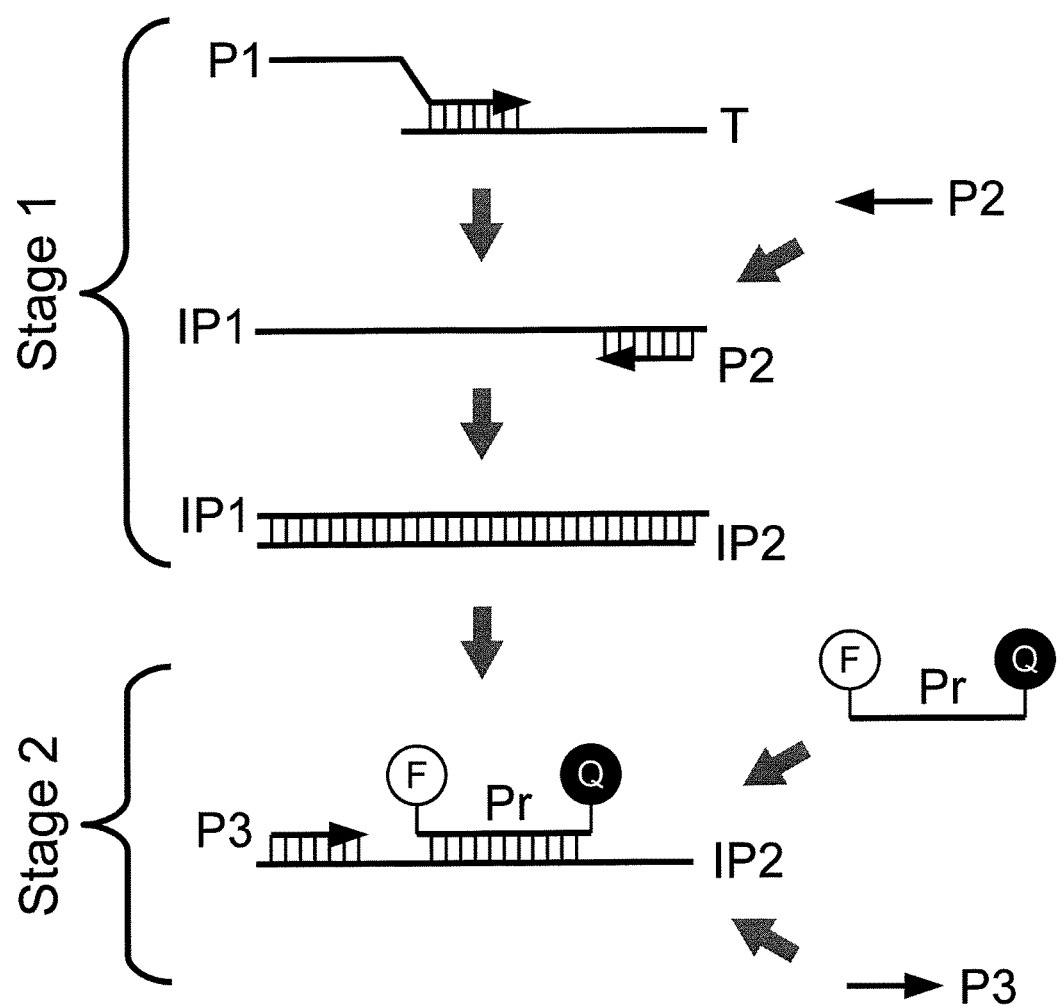
FIG. 8 is a schematic showing one version of a the two-stage single-tube real-time PCR assay.

A novel qPCR scheme was developed that offers high target specificity by utilizing three sequence-specific components, including a TaqMan probe, yet allows for very short amplicons by means of a partial target recognition sequence overlap of the TaqMan probe with the sense (same-strand) target-specific primer. To accommodate the overlapping probe and primer, a novel 2-stage single-tube qPCR scheme was devised. The flow diagram provided in FIG. 8 shows the specific details and steps of the reaction. In FIG. 8, T designates a template; P1, P2, and P3 designate primers; IP1 and IP2 designate intermediate products; Pr designates TaqMan™ probe, dual-labeled with fluorophore F and quencher Q. In stage 1, the target DNA template T is amplified using primers P1 and P2, which map in very close proximity to each other on the target sequence, thus allowing for very short templates. Primer P1 carries a target-unrelated 5'-end extension sequence, which is incorporated into the PCR product IP1/IP2 along with the template sequence. The resulting intermediate PCR product IP2 is sufficiently long to serve as template in stage 2, which involves primers P3 and P2 and a labeled TaqMan probe Pr. The mechanics of stage 2 are largely identical to those of a standard TaqMan qPCR assay. During this stage, as in a standard TaqMan qPCR assay, the amount of the final PCR product is monitored by measuring the increase in fluorescence of the PCR mixture. The three target-specific components in the assay are primers P3 and P2 and the TaqMan probe (Pr). Determination of the annealing temperatures ($T_a$) of the participant oligonucleotides, their concentrations, extension temperatures, and the number of cycles in each stage is an important part of assay development. The resulting assay proved to be exceptionally sensitive, highly sequence-specific, and suitable for the detection of target fragments as short as 20 to 50 bases ("ultra short" targets).

The oligonucleotide components involved in the 2-stage qPCR assay for ultra short targets were designed with the following considerations:

When choosing among potential targets, preference was given to those located in genomic sequence regions of relatively high $T_m$, which allow for the design of correspondingly short primers and probes.

The $T_m$ of the probe Pr-PCR product complex was chosen to be 68° C. to 70° C.

The $T_m$ of the target recognition sequences of primers P2 and P3 were chosen to be 8° C. to 10° C. below that of probe Pr, as they would normally be in a standard TaqMan assay.

The $T_m$ of the target recognition sequence of primer P1 was chosen to be 8° C. to 10° C. below that of primers P2 and P3 to allow control of the length of each stage by altering the annealing/extension phase temperature. This low $T_m$ requirement also allows for very short target recognition sequence of in primer P1, thus reducing the minimum required overall length of the template.

A specific example of this method is an assay developed for the purpose of detecting *M. tuberculosis* sequences in urine DNA samples. The target is a 39-bp region within the IS6110 repeat of the bacteria.

| Direction | ID | Template | SEQ ID |
|---|---|---|---|
| 1st-stage forward primer (P1) | ES0564 | 5'-GAACACGACCTACGACGAGTCAGCA TCTAGCTTCGGACCACCA-3' | 23 |
| reverse primer (P2) | ES0563 | 5'-CTGCTACCCACAGCCGGTTAG-3' | 24 |
| 2nd-stage forward primer (P3) | ES0565 | 5'-CACGACCTACGACGAGTCAGC-3' | 25 |
| TaqMan MGB probe (Pr) | ES0566-M | FAM-5'-TTCGGACCACCAGCAC-3'-MGB-NFQ | 26 |
| MTB target | | 5'-GCTTCGGACCACCAGCACCTAACCG GCTGTGGGTAGCAG-3' | 27 |

Figure 9:
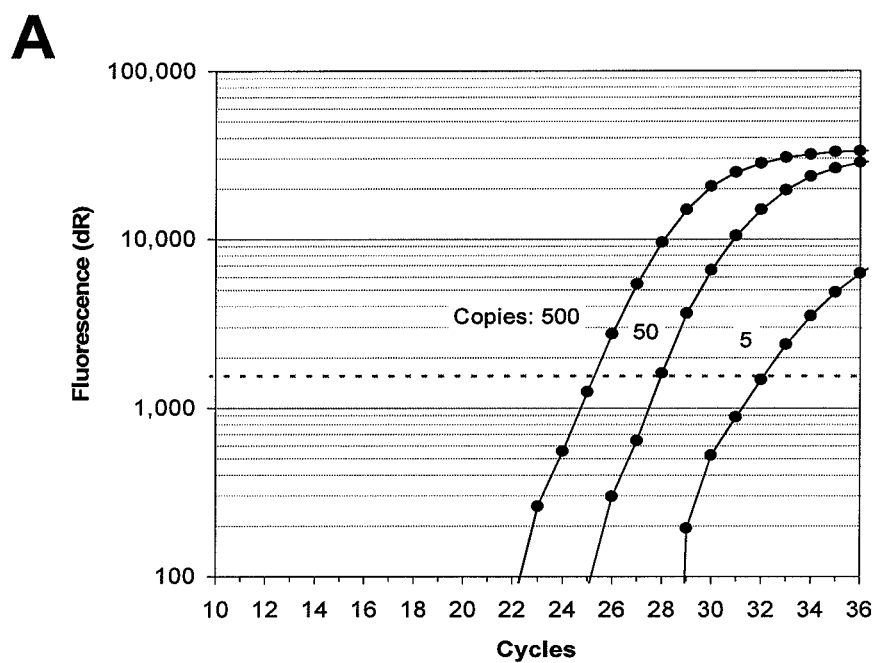
FIG. 9, Panel A, is a graph showing detection of *M. tuberculosis* IS6110 sequences (39-bp target) by the two-stage single-tube real-time PCR assay of FIG. 8. Panel B shows detection of *M. tuberculosis* Tr-DNA in the urine samples from patients with pulmonary tuberculosis and non-infected controls.
Figure 9:
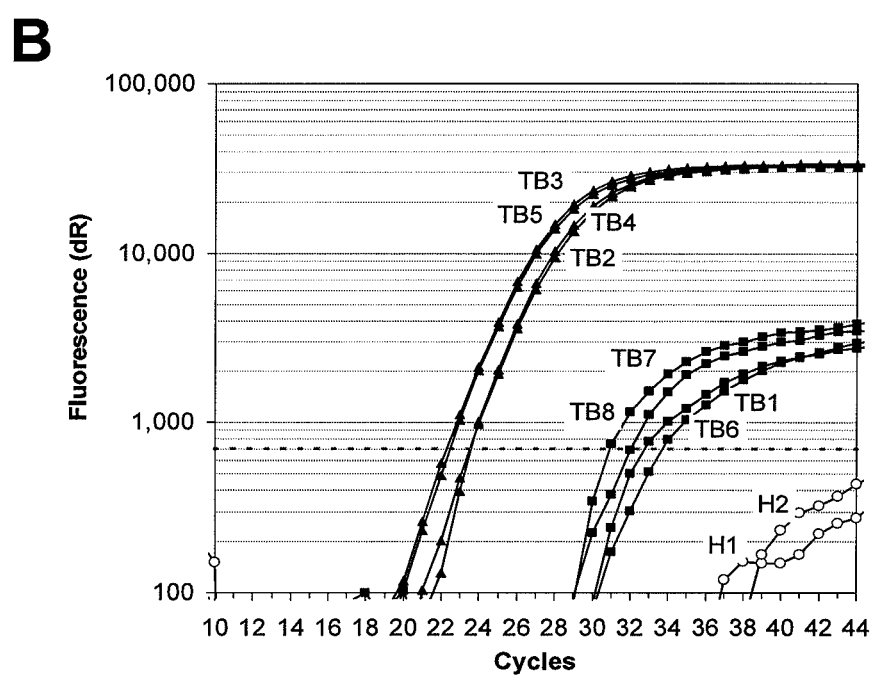

FIG. 9, Panel A, demonstrates that this technique effectively detects 5 genome-equivalents of *M. tuberculosis* per reaction. FIG. 9, Panel B, illustrates application of this test for detection of *M. tuberculosis* Tr-DNA in the urine samples from patients with pulmonary tuberculosis and non-infected controls. Specifically, Panel A shows amplification of IS6110 standards and Panel B shows the detection of IS6110 in DNA from urine samples of 8 tuberculosis patients (TB1 through TB8) and two healthy individuals (H1 and H2).

Example 4

Example 4 shows an alternative design of single-tube PCR scheme for detection of ultra short DNA targets.

Figure 10:
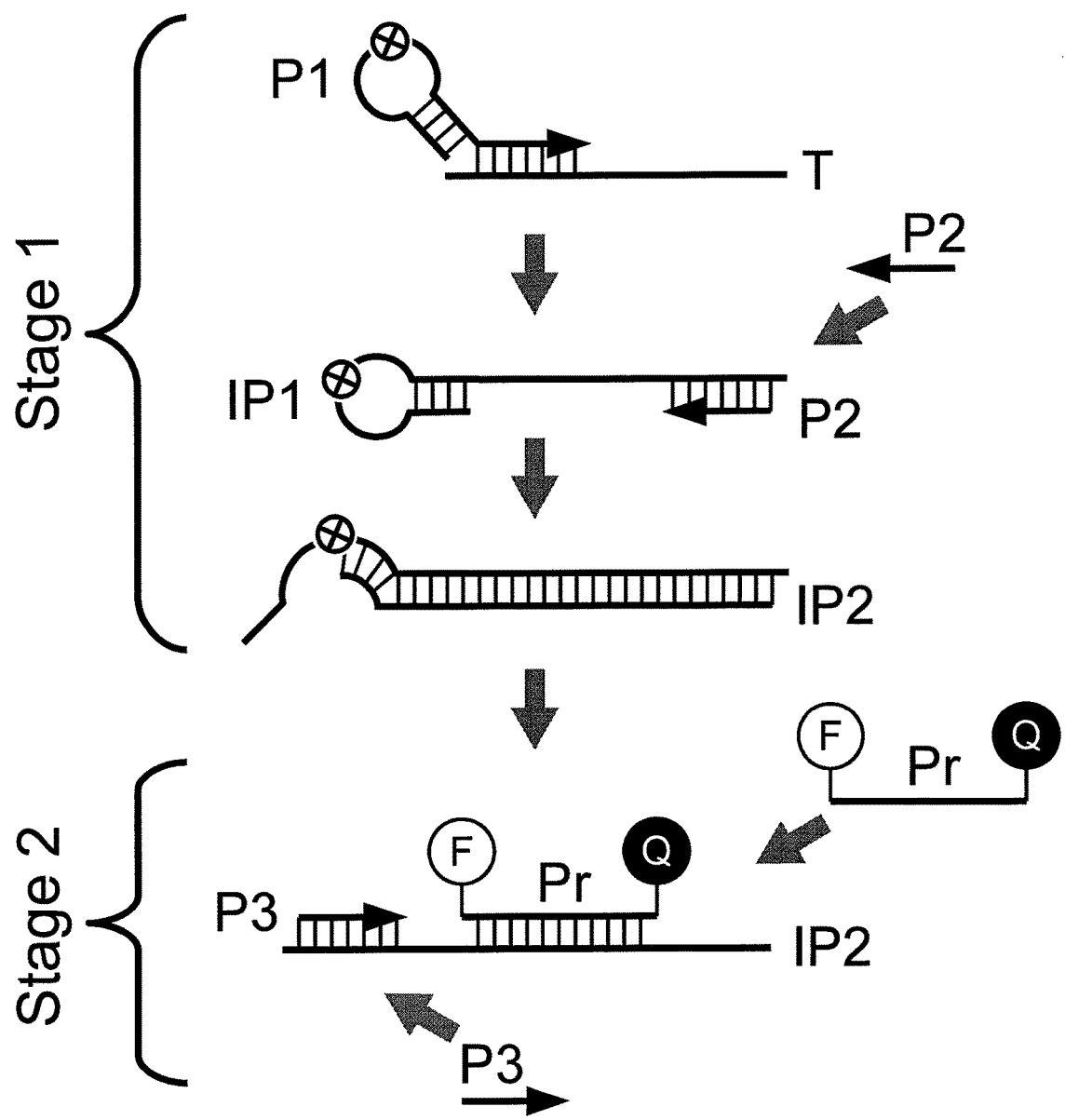
FIG. 10 is a schematic showing a second version of a the two-stage single-tube real-time PCR assay.

In performing the above-described experiments, it was determined that to achieve better linearity of the assay it is important to prevent primer P1 from competing for template with probe Pr in stage 2 of the reaction. To that end, primer P1 was modified in such a way that it preferentially exists in a folded, stem-loop configuration at the annealing/extension phase temperature(s) of stage 2. As shown in FIG. 10, to prevent the stem-loop region from being copied into the PCR product, an iso-dC replication-blocking base was introduced into the loop part of primer P1. In FIG. 10, T designates a template; P1, P2, and P3 designate primers; IP1 and IP2 designate intermediate products; Pr designates TaqMan™ probe, dual-labeled with fluorophore F and quencher Q. (x) designates iso-dC.

The 2-stage Real-Time PCR assay has been shown to be able to detect a number of various targets. For each target, a custom set of primer and probe sequences were designed, and the physical conditions of the assay were optimized. The optimized factors included $Mg^{2+}$ concentration, primers and probe concentrations, the temperatures of the annealing/extension phase for each stage, and the length (i.e., the number of amplification cycles) of stage 1. The responses of the system which were optimized included assay sensitivity, specificity, and linearity. It was found that the 2-stage qPCR assay can be used to reliably detect ultra short targets at concentrations as low as 1 to 5 copies per reaction.

Figure 11:
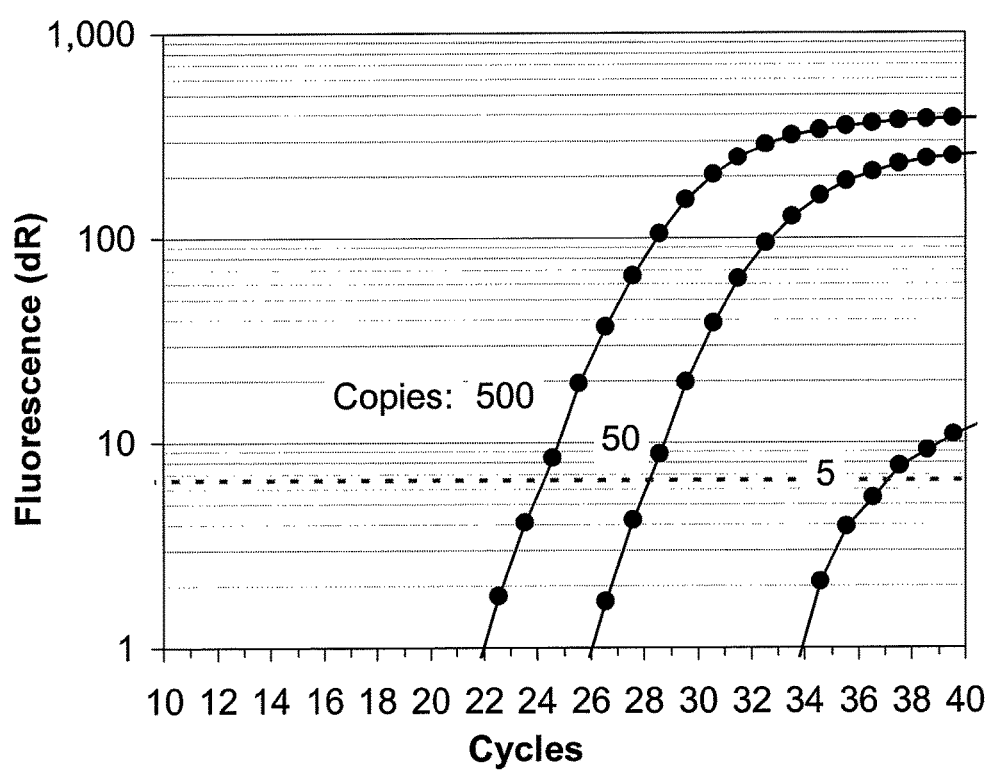
FIG. 11 is a graph showing amplification of SRY standards (25-bp target) by the two-stage single-tube real-time PCR assay of FIG. 10.
Figure 12:
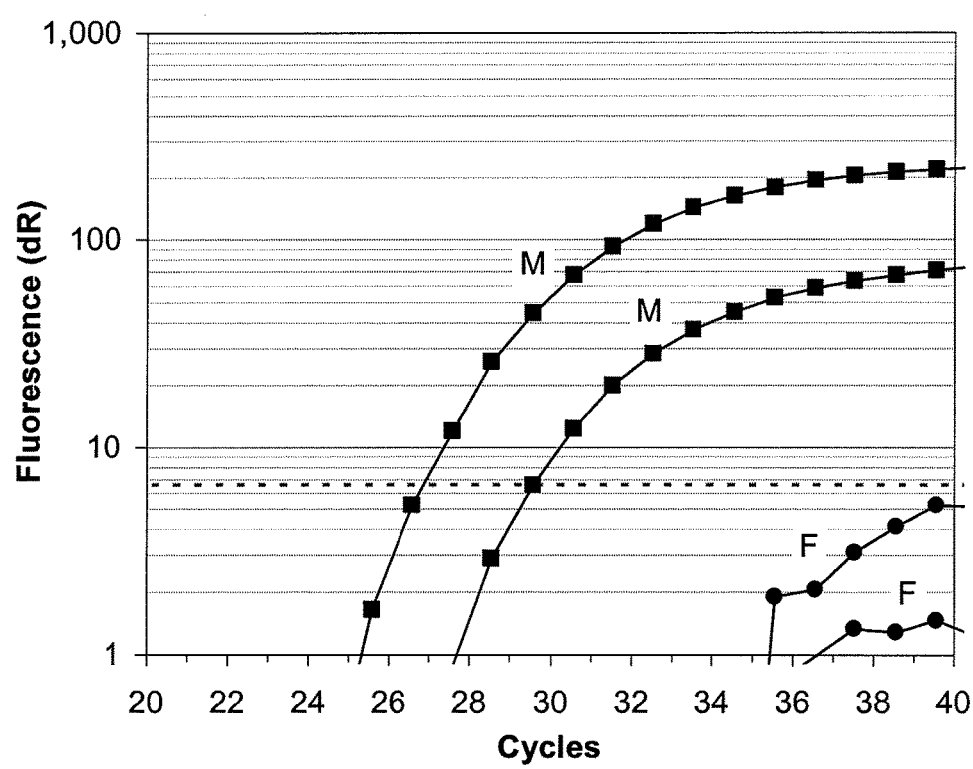
FIG. 12 is a graph showing fetal gender detection of DNA extracted from urine of pregnant women by the two-stage single-tube real-time PCR assay of FIG. 10.

One such 2-stage Real-Time PCR system was designed to detect 25-bp SRY target. The amplification curves of the standard concentration of positive control template are shown in FIG. 11. FIG. 12 illustrates detection of fetal SRY sequences in DNA isolated from urine of women pregnant with male but not with female fetuses. In FIG. 12, M and F designate samples from women pregnant with male and female fetuses, respectively.

Example 5

Example 5 shows the detection of fetal sequences of different size in DNA isolated from maternal urine by two methods.

Figure 13:
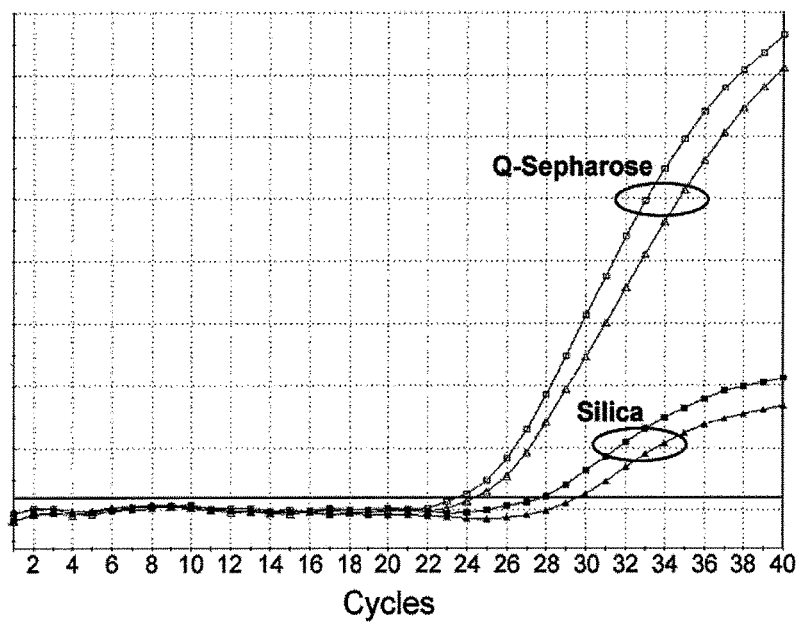
FIG. 13 is a graph showing a detection comparison of Y chromosome-specific TSPY sequences (43-bp target) in urinary DNA purified by Q-Sepharose and silica methods by the two-stage single-tube real-time PCR assay of FIG. 8.

DNA from the urine from women pregnant with male fetuses was isolated both by the silica-based method of Botezatu et al., Clin Chem. 46:1078-1084, 2000 and by the anion exchanger-based technique described in U.S. Patent Application Publication No. 20080139801. The isolated DNA was then analyzed for the presence of Y chromosome-specific TSPY sequences by real time PCR using primers designed for detection of 84 base pairs and ultra short 43 base pairs targets. The silica-based method isolates 100-150 base pairs DNA fragments and larger. The anion-exchanger-based technique isolates DNA fragments larger than 10 base pairs. Independent of the DNA purification method, the male-specific sequences were successfully detected in urinary DNA using the 43 base pairs amplicon assay, but not the 84 base pairs assay. Furthermore, FIG. 13 demonstrates that the detected amount of TSPY sequences in Q-Separose preparation was twice as high as that in the silica preparation.

The next experiments were designed to characterize fetal Tr-DNA in more details. Using four sets of primers and probes, which amplified 25 base pairs, 39 base pairs, 65 base pairs, and 88 base pairs sequences of the SRY gene, real time PCR was performed with DNA isolated from the same urine specimens of women pregnant with male fetuses by two techniques, based on the silica or Q-resin absorption. Data presented in the following table clearly demonstrate that both factors are very important, a method of DNA isolation and the amplicon size. First, sensitivity is higher with shorter amplicon size. Even the increase of a target sequence size from 25 base pairs to 39 base pairs decreased test sensitivity, and fetal DNA was undetectable in all samples with 88 base pairs amplicon. Second, isolation of DNA fragments shorter than 150 base pairs with the Q-resin-based technique significantly increased sensitivity when 25 base pairs and 39 base pairs sequences were amplified. Both DNA isolation methods gave similar results with the 65 base pairs amplicon.

Numbers of successfully detected pregnancies with male fetuses depending on the amplicon size. DNA was isolated by two methods from urine samples of ten women pregnant with male fetuses.

| DNA isolation method | Size of SRY target | | | |
|---|---|---|---|---|
| | 25 base pairs | 39 base pairs | 65 base pairs | 88 base pairs |
| Q-resin | 10 | 8 | 3 | 0 |
| Silica | 7 | 4 | 3 | 0 |

Data obtained provide information on properties of Tr-DNA, in particular characteristics of fetal Tr-DNA in the maternal urine. First, higher sensitivity of detection of fetal sequence in DNA purified with Q-resin when compared to DNA isolated by the silica method demonstrates that 50-<150 base pairs DNA fragments contain fetal Tr-DNA. This difference in sensitivity is seen with 25 base pairs and 39 base pairs amplicons only, which means that larger fragments of fetal Tr-DNA detectable with 65 base pairs amplicon belong to DNA fractions isolated by both methods, most likely to 150-200 base pairs DNA fragments.

Second, sensitivity of detection of fetal sequences in DNA isolated with the silica method depends on the amplicon size in a size range of 25-88 base pairs, although the shortest DNA fragments isolated by this technique are about 150 base pairs long. The most plausible explanation of these results is the presence of single-strand breaks in 150-200 base pairs fragments of Tr-DNA, which makes amplifiable targets significantly shorter.

Based on the foregoing results, detection of ultra short DNA targets is essential to the successful detection of Tr-DNA sequences.

Example 6

Example 6 shows the detection of bacterial transrenal DNA sequences of different size in DNA isolated from urine of tuberculosis patients by two methods.

Since bacterial DNA is covered by different proteins than eukaryotic DNA and is not packed in nucleosomes, data obtained with human Tr-DNA are not necessarily correct for prokaryotic DNA. Recently, *Mycobacterium tuberculosis* (MTB) DNA was detected by means of nested PCR in the urine from pulmonary tuberculosis patients (Cannas, A. et al., Int. J. Tuberc. Lung Dis. 12: 146-151, 2008). In the first set of experiments with MTB DNA, urinary DNA was isolated by the two methods described above and analyzed by real time PCR using primers designed for amplicons of various sizes. The table below demonstrates that bacterial Tr-DNA fragments can be detected in the urine from infected patients by amplification of short and ultra short targets, but in the latter case a significantly higher number of MTB-specific gene copies are detected. Still more copies of the MTB DNA sequences were detected with primers designed for ultra short targets in DNA preps isolated by anion exchanger-based methods.

Amplicon size dependence of MTB Tr-DNA detection (copies/ml) in nucleic acids isolated by two methods from urine of a patient with active pulmonary tuberculosis.

| Target Size | Silica | Q-Sepharose |
|---|---|---|
| 39 base pairs | 24 | 50 |
| 49 base pairs | 5 | 4 |
| 99 base pairs | 0 | 0 |

Example 7

Example 7 shows the detection of prokaryotic and eukaryotic transrenal DNA in fractionated urinary DNA.

Figure 14:
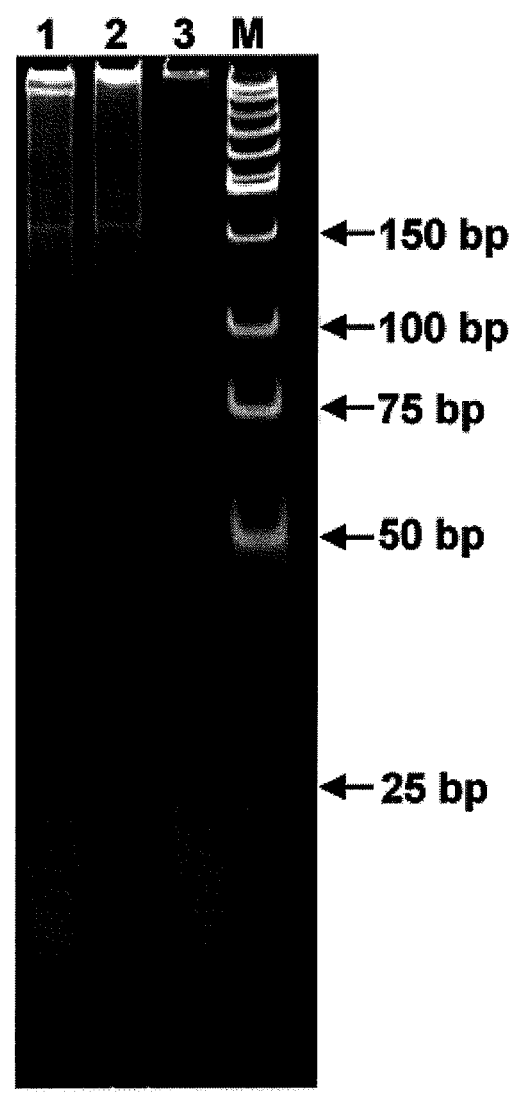
FIG. 14 is a photograph of a silica gel showing separation of high/medium and low molecular weight urinary nucleic acids based on their differential retention by silica in the presence of ethanol.

Nucleic acids isolated from urine were further separated into high/medium and low molecular weight fractions. Ethanol was added to nucleic acids eluted from the Q-Sepharose to 30% v/v, and the mixture was passed through a silica column. A flow-through fraction was collected, and after the addition of ethanol up to 70% the mixture was loaded onto another silica column. High/medium and low molecular weight nucleic acids, respectively, were eluted from the first and the second columns. FIG. 14 illustrates separation of urinary nucleic acids of different molecular weights. In FIG. 14, Lane 1 shows total nucleic acids; Lane 2 shows high/medium molecular weight fraction and Lane 3 shows low molecular weight fractions.

In the first set of experiments, the amount of Y chromosome-specific TSPY and SRY sequences in the high/medium and in low molecular weight fractions was compared. Data presented in the following table demonstrate that the latter contained the significant amount of fetus-specific sequences.

Concentrations of fetal Tr-DNA in nucleic acid fractions from urine of a woman pregnant with a male fetus.

| DNA | TSPY GE/ml of urine | SRY GE/ml of urine |
|---|---|---|
| Total DNA | 44 | 67 |
| High/medium MW | 3 | 19 |
| Low MW | 33 | 61 |

Figure 15:
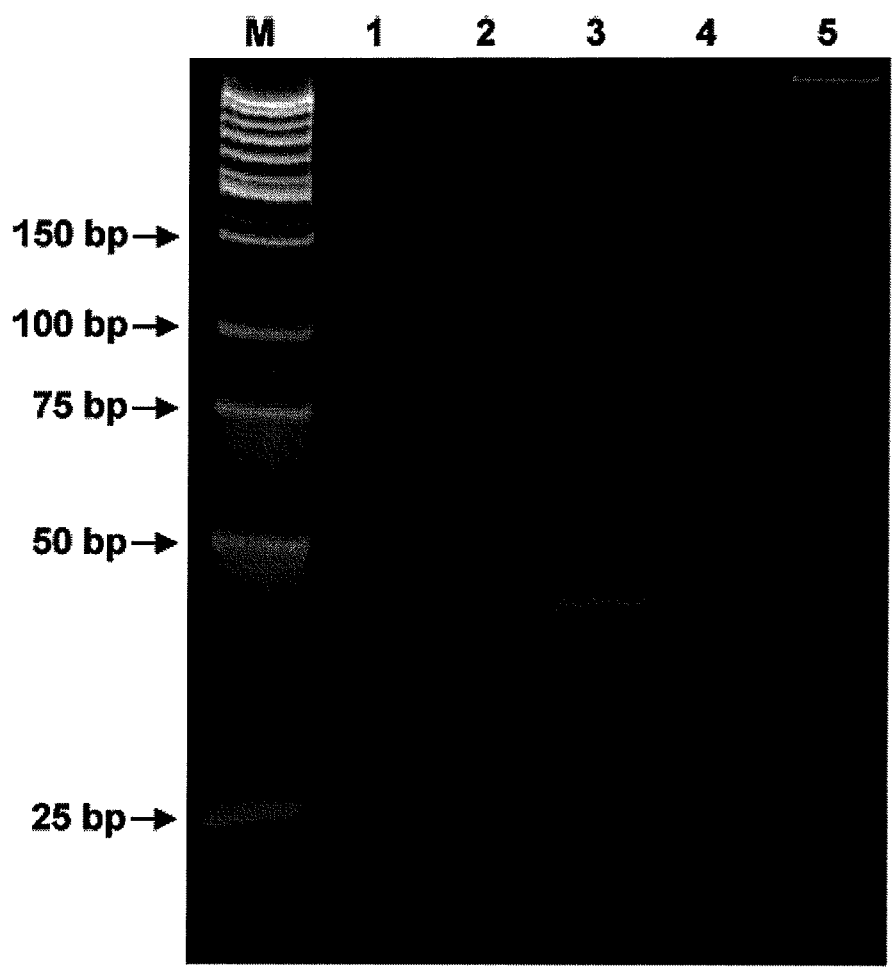
FIG. 15 is a photograph of a silica gel showing comparing abundance of MTB-specific templates in fractionated nucleic acids purified from the urine of a patient with active pulmonary tuberculosis.

Similar experiments were performed for analysis of bacterial Tr-DNA distribution in fractionated urinary DNA. The results of MTB DNA analysis in fractionated DNA from the urine of a patient with pulmonary tuberculosis are presented in FIG. 15. In FIG. 15, Lane 1 shows total DNA; Lane 2 shows high/medium molecular weight DNA; Lane 3 shows low molecular weight DNA; Lane 5 shows no template (control reaction); and Lane 5 shows positive control with MTB genomic DNA (Erdman strain).

Once again, MTB-specific sequences were detected in both high/medium and low molecular weight fraction, the latter contains more copies of bacterial Tr-DNA.

What is claimed is:

1. A method comprising
   (a) obtaining a urine sample from a patient;
   (b) isolating DNA smaller than 1000 base pairs from the urine sample; and
   (c) analyzing said DNA for one or more gene sequence, wherein the gene sequence is specifically amplified using polymerase chain reaction (PCR) to produce an amplicon less than 50 nucleotides in length that comprises a portion of the DNA isolated in step (b),
   wherein said PCR uses a primer pair comprising two primers that are each sufficiently complementary to hybridize with a target binding sequence of the mutant gene sequence or its complement,
   wherein both primers of said primer pair are sufficiently complementary to the mutant gene sequence or its complement at said primers' 3' portion to hybridize thereto, and said both primers further comprise nucleotide fragments at the 5' end of both primers that are not sufficiently complementary to the mutant gene sequence or its complement to hybridize thereto,
   wherein
      the nucleotide fragment at the 5' end of one primer of said primer pair comprises a donor fluorophore;
      the nucleotide fragment at the 5' end of the other primer of said primer pair comprises an acceptor fluorophore; and
      the nucleotide fragments at the 5' ends of both primers of said primer pair are complementary to each other, such that the acceptor and donor are in proximity to cause acceptor fluorescence by Förster resonance energy transfer (FRET) in the amplicon, and
   wherein the gene sequence is part of a cell-free genomic DNA fragment that has crossed the kidney barrier.

2. The method of claim 1, wherein DNA smaller than 300 base pairs is isolated from the urine samples.

3. The method of claim 1, wherein the amplicon is less than 45 nucleotides.

4. The method of claim 1, wherein the amplicon is less than 40 nucleotides.

5. The method of claim 1, wherein the amplicon is less than 35 nucleotides.

6. The method of claim 1, wherein the DNA smaller than 1000 base pairs is isolated using an anion exchange resin.

7. The method of claim 6, wherein the anion exchange resin is Q-Sepharose.

8. A method comprising
   (a) obtaining a urine sample from a patient;
   (b) isolating DNA smaller than 1000 base pairs from the urine sample; and
   (c) analyzing said DNA for one or more gene sequence, wherein the gene sequence is specifically amplified using polymerase chain reaction (PCR) to produce an amplicon less than 50 nucleotides in length that comprises a portion of the DNA isolated in step (b),
   wherein said PCR uses a primer pair comprising two primers that are each sufficiently complementary to hybridize with a target binding sequence of the mutant gene sequence or its complement,
   wherein both primers of said primer pair are sufficiently complementary to the mutant gene sequence or its complement at said primers' 3' portion to hybridize thereto, and said both primers further comprise nucleotide fragments at the 5' end of both primers that are not sufficiently complementary to the mutant gene sequence or its complement to hybridize thereto,
   wherein
      said nucleotide fragment at the 5' end of said at least one primer is internally complementary such that it forms a stem-loop configuration, wherein the loop part of said stem-loop comprises a replication-blocking base and forms an intermediate product IP1 when it binds to the mutant gene sequence and is extended by a polymerase;
      the other primer of said primer pair forms an intermediate product IP2 when it binds to Ip1 and is extended by a polymerase to the replication blocking base; and
      a labeled TaqMan probe Pr that is complementary to IP2 and comprises a fluorophore and quencher, is fragmented, allowing fluorescence from the fluorophore, when a third primer complementary to a region of IP2 that binds to IP2 in a region of IP2 that is 3' from Pr, is extended by a polymerase, and wherein the gene sequence is part of a cell-free genomic DNA fragment that has crossed the kidney barrier.

9. The method of claim 8, wherein DNA smaller than 300 base pairs is isolated from the urine samples.

10. The method of claim 8, wherein the amplicon is less than 45 nucleotides.

11. The method of claim 8, wherein the amplicon is less than 40 nucleotides.

12. The method of claim 8, wherein the amplicon is less than 35 nucleotides.

13. The method of claim 8, wherein the amplicon is less than 30 nucleotides.

14. The method of claim 8, wherein the DNA smaller than 1000 base pairs is isolated using an anion exchange resin.

15. The method of claim 14, wherein the anion exchange resin is Q-Sepharose.

16. The method of claim 8, wherein the gene sequence is chromosome Y-specific.

17. The method of claim 15, wherein the chromosome Y-specific gene sequence is an SRY sequence.

18. The method of claim 16, wherein the SRY sequence is 25 base pairs.

* * * * *